US012797215B2

(12) United States Patent
Folan et al.

(10) Patent No.: US 12,797,215 B2
(45) Date of Patent: Nov. 17, 2026

(54) REMOVABLE STENT

(71) Applicant: BOSTON SCIENTIFIC SCIMED, INC., Maple Grove, MN (US)

(72) Inventors: Martyn G. Folan, Galway (IE); Geraldine Toner, Raphoe (IE); Daniel Tuck, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 296 days.

(21) Appl. No.: 18/767,163

(22) Filed: Jul. 9, 2024

(65) Prior Publication Data

US 2024/0358532 A1 Oct. 31, 2024

Related U.S. Application Data

(63) Continuation of application No. 18/306,124, filed on Apr. 24, 2023, now Pat. No. 12,053,399, which is a (Continued)

(51) Int. Cl.
*A61F 2/95* (2013.01)
*A61F 2/04* (2013.01)

(52) U.S. Cl.
CPC .......... *A61F 2/95* (2013.01); *A61F 2002/045* (2013.01); *A61F 2002/9528* (2013.01); *A61F 2250/001* (2013.01); *A61F 2250/0059* (2013.01)

(58) Field of Classification Search
CPC ................ A61F 2/95; A61F 2002/9528; A61F 2002/9511; A61F 2002/9534; A61F 2002/9665; A61F 2/2427; A61F 2/243; A61F 2/2466; A61F 2/07; A61F 2002/9505; A61F 2/844; A61F 2/90; A61F 2250/0039; A61F 2/966
See application file for complete search history.

(56) References Cited

U.S. PATENT DOCUMENTS 5,238,004 A 8/1993 Sahatjian et al.
5,779,732 A * 7/1998 Amundson ............. A61F 2/958 606/198

(Continued)

FOREIGN PATENT DOCUMENTS

EP 1518518 A2 3/2005
EP 1870057 A1 12/2007

OTHER PUBLICATIONS

International Search Report and Written Opinion for International Application No. PCT/US2019/035239, dated Aug. 16, 2019. (11 pages).

*Primary Examiner* — Seema Mathew
(74) *Attorney, Agent, or Firm* — Seager, Tufte & Wickhem, LLP

(57) ABSTRACT

An illustrative endoluminal implant having an elongated tubular member. The elongate tubular member having a proximal stent, a distal stent and an interconnecting sleeve. The proximal stent tapers from a first outer diameter adjacent the proximal end region to a second smaller outer diameter adjacent the distal end region. The distal stent has an outer diameter less than the first outer diameter of the proximal stent. The interconnecting sleeve is collapsible in response to an applied radial force such that the sleeve is positionable across a natural valve or sphincter.

16 Claims, 14 Drawing Sheets

Related U.S. Application Data continuation of application No. 16/430,147, filed on Jun. 3, 2019, now Pat. No. 11,660,216.

(60) Provisional application No. 62/680,175, filed on Jun. 4, 2018.

(56) References Cited

U.S. PATENT DOCUMENTS

| | | | | |
|---|---|---|---|---|
| 5,984,957 | A | 11/1999 | Laptewicz, Jr. et al. | |
| 6,165,214 | A | 12/2000 | Lazarus | |
| 6,508,803 | B1 | 1/2003 | Horikawa et al. | |
| 6,669,724 | B2 | 12/2003 | Park et al. | |
| 6,974,471 | B2 | 12/2005 | Van Schie et al. | |
| 7,252,680 | B2 | 8/2007 | Freitag | |
| 7,731,742 | B2 | 6/2010 | Schlick et al. | |
| 8,372,134 | B2 | 2/2013 | Schlick et al. | |
| 8,398,699 | B2 | 3/2013 | Shin et al. | |
| 8,414,635 | B2 | 4/2013 | Hyodoh et al. | |
| 8,876,880 | B2 | 11/2014 | Hyodoh et al. | |
| 8,968,384 | B2 * | 3/2015 | Pearson | A61F 2/954 623/1.13 |
| 9,050,168 | B2 | 6/2015 | Neisz et al. | |
| 9,173,760 | B2 | 11/2015 | Belhe et al. | |
| 9,301,862 | B2 | 4/2016 | Jordan et al. | |
| 9,554,924 | B2 | 1/2017 | Schlick et al. | |
| 9,801,749 | B2 | 10/2017 | Hingston et al. | |
| 9,872,758 | B2 | 1/2018 | Schlick et al. | |
| 10,028,850 | B2 | 7/2018 | Tupil et al. | |
| 10,231,819 | B2 * | 3/2019 | Liddy | B05D 1/18 |
| 10,251,767 | B1 * | 4/2019 | Sedghi | A61B 5/7455 |
| 10,278,848 | B1 * | 5/2019 | Slazas | A61F 2/95 |
| 10,314,685 | B2 * | 6/2019 | McMahon | A61F 2/04 |
| 10,390,982 | B1 * | 8/2019 | Raychev | A61F 2/90 |
| 10,987,234 | B2 * | 4/2021 | Robison | A61F 2/856 |
| 11,123,174 | B2 * | 9/2021 | Burkart | A61F 2/07 |
| 11,147,572 | B2 * | 10/2021 | Vale | A61B 17/221 |
| 11,166,806 | B2 * | 11/2021 | Johnson | A61F 2/04 |
| 11,253,379 | B2 * | 2/2022 | Fulkerson | A61L 31/16 |
| 11,432,952 | B2 * | 9/2022 | Sondreaal | A61F 2/97 |
| 11,439,492 | B2 * | 9/2022 | Walzman | A61M 25/0021 |
| 11,850,149 | B2 * | 12/2023 | Walsh | A61F 2/2418 |
| 11,883,310 | B2 | 1/2024 | Nolan et al. | |
| 2002/0099431 | A1 * | 7/2002 | Armstrong | A61F 2/958 623/1.11 |
| 2002/0143387 | A1 * | 10/2002 | Soetikno | A61F 2/95 623/1.15 |
| 2004/0039452 | A1 | 2/2004 | Bessler | |
| 2004/0102855 | A1 * | 5/2004 | Shank | A61F 2/90 623/23.68 |
| 2006/0095117 | A1 | 5/2006 | Popelar et al. | |
| 2006/0095119 | A1 * | 5/2006 | Bolduc | A61B 17/064 623/1.36 |
| 2006/0142836 | A1 | 6/2006 | Hartley et al. | |
| 2006/0161187 | A1 * | 7/2006 | Levine | A61F 5/0076 606/153 |
| 2006/0190075 | A1 | 8/2006 | Jordan et al. | |
| 2006/0224235 | A1 | 10/2006 | Rucker | |
| 2006/0253190 | A1 * | 11/2006 | Kuo | A61F 2/07 623/1.44 |
| 2006/0276887 | A1 | 12/2006 | Brady et al. | |
| 2007/0100427 | A1 | 5/2007 | Perouse | |
| 2007/0219619 | A1 * | 9/2007 | Dieck | A61F 2/07 623/1.13 |
| 2007/0233230 | A1 | 10/2007 | Nissl et al. | |
| 2008/0109087 | A1 | 5/2008 | Durgin | |
| 2008/0125845 | A1 | 5/2008 | Fischer et al. | |
| 2009/0099640 | A1 * | 4/2009 | Weng | A61F 2/95 623/1.11 |
| 2010/0049294 | A1 | 2/2010 | Zukowski et al. | |
| 2010/0094327 | A1 * | 4/2010 | Milsom | A61B 17/0218 606/191 |
| 2010/0280591 | A1 * | 11/2010 | Shin | A61F 2/90 623/1.15 |
| 2010/0280592 | A1 * | 11/2010 | Shin | A61F 2/90 623/1.15 |
| 2010/0316830 | A1 * | 12/2010 | Hartley | A61F 2/07 428/64.1 |
| 2011/0060398 | A1 * | 3/2011 | Tupil | A61F 2/86 623/1.15 |
| 2011/0087320 | A1 * | 4/2011 | Bolduc | A61F 2/07 623/1.35 |
| 2011/0152920 | A1 * | 6/2011 | Eckhouse | A61B 17/221 606/200 |
| 2011/0160836 | A1 * | 6/2011 | Behan | A61F 2/95 623/1.11 |
| 2011/0245851 | A1 * | 10/2011 | Ducharme | A61B 17/0057 606/151 |
| 2011/0264192 | A1 * | 10/2011 | Hartley | A61F 2/07 623/1.13 |
| 2011/0307070 | A1 | 12/2011 | Clerc et al. | |
| 2012/0041538 | A1 * | 2/2012 | White | A61F 2/90 623/1.12 |
| 2012/0253454 | A1 * | 10/2012 | Costello | A61F 2/90 623/1.34 |
| 2012/0290072 | A1 * | 11/2012 | Theobald | A61F 2/82 623/1.15 |
| 2012/0310363 | A1 * | 12/2012 | Gill | A61F 2/07 623/23.7 |
| 2013/0123896 | A1 * | 5/2013 | Bloss | A61F 2/95 623/1.11 |
| 2013/0245742 | A1 | 9/2013 | Norris | |
| 2014/0277573 | A1 * | 9/2014 | Gill | A61F 2/2476 623/23.68 |
| 2014/0364959 | A1 * | 12/2014 | Attar | A61F 2/04 623/23.7 |
| 2015/0282922 | A1 * | 10/2015 | Hingston | A61F 2/04 623/23.7 |
| 2016/0081832 | A1 | 3/2016 | Hingston et al. | |
| 2016/0184118 | A1 | 6/2016 | Faber et al. | |
| 2016/0206449 | A1 | 7/2016 | Mort et al. | |
| 2016/0270935 | A1 | 9/2016 | Rasmussen et al. | |
| 2017/0056224 | A1 | 3/2017 | Baxter et al. | |
| 2017/0290653 | A1 | 10/2017 | Folan et al. | |
| 2017/0325983 | A1 | 11/2017 | Valdes et al. | |
| 2018/0036113 | A1 | 2/2018 | Burkart et al. | |
| 2019/0365549 | A1 * | 12/2019 | Folan | A61F 2/04 |
| 2019/0388256 | A1 * | 12/2019 | Chung | A61F 2/07 |
| 2020/0093622 | A1 * | 3/2020 | Nolan | A61F 2/848 |
| 2020/0214858 | A1 | 7/2020 | Gilmartin et al. | |
| 2021/0228389 | A1 * | 7/2021 | Smith | A61F 2/966 |
| 2022/0023073 | A1 | 1/2022 | Shirahama | |
| 2022/0354639 | A1 * | 11/2022 | Haribabu | A61F 2/2466 |

* cited by examiner

REMOVABLE STENT

CROSS-REFERENCE TO RELATED APPLICATIONS

This application is a continuation of U.S. patent application Ser. No. 18/306,124, filed Apr. 24, 2023, which is a continuation of U.S. patent application Ser. No. 16/430,147, filed Jun. 3, 2019, now U.S. Pat. No. 11,660,216, which claims the benefit of priority of U.S. Provisional Application No. 62/680,175, filed Jun. 4, 2018, the entire disclosure of which is hereby incorporated by reference.

TECHNICAL FIELD

The present disclosure relates generally to methods and apparatuses for various digestive ailments. More particularly, the disclosure relates to removable stents for extending through a valved region.

BACKGROUND

Implantable stents are devices that are placed in a tubular body structure, such as a blood vessel, esophagus, trachea, biliary tract, colon, intestine, stomach or body cavity, to provide support and to maintain the structure open. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery/retrieval devices as well as alternative methods for manufacturing and using medical devices and delivery/retrieval devices.

SUMMARY

This disclosure is directed to several alternative designs, materials, methods of manufacturing medical device structures and associated uses thereof, such as stents for preventing leaks after an anastomosis surgery and/or treating various gastro-intestinal, digestive, or other ailments.

One illustrative embodiment is an implant including a first region, a second region and a third region. The first region has a proximal end region and a distal end region. The first region includes a flared proximal stent frame tapering radially inward in a distal direction. The second region has a proximal end region and a distal end region. The second region includes a flexible sleeve extending distally from the distal end region of the first region. The third region has a proximal end region and a distal end region. The third region includes a distal stent frame having an outer diameter less than an outer diameter of the flared proximal stent frame adjacent the proximal end region of the first region and extending distally from the distal end region of the second region. The flexible sleeve is configured to extend across a natural valve or sphincter and collapse upon itself in response to a radially applied force.

Additionally or alternatively, in another embodiment the implant includes a first retrieval suture configured to at least partially collapse the implant for removal from a body lumen.

Additionally or alternatively, in another embodiment the first retrieval suture is interwoven with the flared proximal stent frame and the distal stent frame.

Additionally or alternatively, in another embodiment the first retrieval suture includes a first suture loop interwoven with the flared proximal stent frame adjacent the proximal end region of the first region, a second suture loop interwoven with the distal stent adjacent the proximal end region of the third region, and a connecting suture portion extending between and coupled to the first and second suture loops.

Additionally or alternatively, in another embodiment a proximal force exerted on the first retrieval suture is configured to partially collapse the flared proximal stent frame adjacent the proximal end region of the first region.

Additionally or alternatively, in another embodiment once the outer diameter of the flared proximal stent frame adjacent the proximal end region of the first region is partially collapsed, the distal stent frame is configured to begin collapsing simultaneously with further collapsing of the proximal stent frame.

Additionally or alternatively, in another embodiment the connecting suture portion includes a slack portion which is configured to be drawn taut as the flared proximal stent frame is partially collapsed before the distal stent frame begins to collapse.

Additionally or alternatively, in another embodiment the first retrieval suture includes a first suture loop interwoven with the distal stent frame adjacent the distal end region of the third region, a second suture loop interwoven with the flared proximal stent frame adjacent the distal end region of the first region, and a connecting suture portion extending between and coupled to the first and second suture loops.

Additionally or alternatively, in another embodiment a distal force exerted on the first retrieval suture is configured to partially collapse the distal stent frame adjacent the distal end region of the third region.

Additionally or alternatively, in another embodiment the connecting suture portion includes a slack portion which is configured to be drawn taut as the distal stent frame is partially collapsed before the flared proximal stent frame begins to collapse.

Additionally or alternatively, in another embodiment the implant includes a second retrieval suture.

Additionally or alternatively, in another embodiment the second retrieval suture is interwoven with the flared proximal stent frame and the distal stent frame.

Additionally or alternatively, in another embodiment at least one of the first or second retrieval sutures is configured to at least partially collapse the flared proximal stent frame prior to collapsing the distal stent frame.

Additionally or alternatively, in another embodiment at least one of the first or second retrieval sutures is configured to at least partially collapse the distal stent frame prior to collapsing the flared proximal stent frame.

Additionally or alternatively, in another embodiment the flared proximal stent frame has an outer profile configured to conform to an outlet of a stomach.

Additionally or alternatively, in another embodiment the outer diameter of the flared proximal stent frame adjacent the proximal end region of the first region is in the range of about 25 millimeters (mm) to about 50 mm.

Additionally or alternatively, in another embodiment the outer diameter of the distal stent frame is in the range of about 15 millimeters (mm) to about 25 mm.

Another illustrative embodiment is an implant including an elongated tubular member. The elongated tubular member includes a proximal stent, a flexible sleeve, and a distal stent. The proximal stent has a proximal end region and a distal end region. The proximal stent tapers from a first outer diameter adjacent the proximal end region to a second smaller outer diameter adjacent the distal end region. The flexible sleeve has a proximal end region and a distal end region. The flexible sleeve extends distally from the distal end region of the flared proximal stent. The distal stent has a proximal end region and a distal end region. The distal stent has an outer diameter less than the first outer diameter of the proximal stent and extends distally from the distal end region of the flexible sleeve. A first retrieval suture is interwoven with the proximal stent and the distal stent. The flexible sleeve is configured to extend across a natural valve or sphincter and collapse upon itself in response to an applied radial force.

Additionally or alternatively, in another embodiment the proximal stent is configured to be positioned at a gastric outlet of a stomach and the flexible sleeve is configured to be positioned across a pyloric sphincter.

Additionally or alternatively, in another embodiment the applied radial force is a natural action of the pyloric sphincter.

Additionally or alternatively, in another embodiment the first retrieval suture is configured to at least partially collapse the proximal stent prior to begin collapsing the distal stent.

Additionally or alternatively, in another embodiment the first retrieval suture is configured to at least partially collapse the distal stent prior to begin collapsing the proximal stent.

Another illustrative embodiment is a method of removing or repositioning an endoluminal implant. The method includes actuating an end of a retrieval suture in a first direction. The retrieval suture is interwoven within an end region of a first stent of an endoluminal implant and an end region of a second stent of the endoluminal implant. The first and second stents are separated and connected by a flexible polymeric sleeve. The end region of the first stent is configured to partially collapse before the end of the second stent begins to collapse.

Additionally or alternatively, in another embodiment the retrieval suture includes a first circumferential loop extending around the end region of the first stent, a second circumferential loop extending around the end of the second stent, and a connecting suture portion extending between the first circumferential loop and the second circumferential loop, wherein a slack portion of the connecting suture portion is drawn taut as the end region of the first stent is partially collapsed before the end of the second stent begins to collapse.

Additionally or alternatively, in another embodiment the first stent is connected to the second stent only by the flexible polymeric sleeve.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
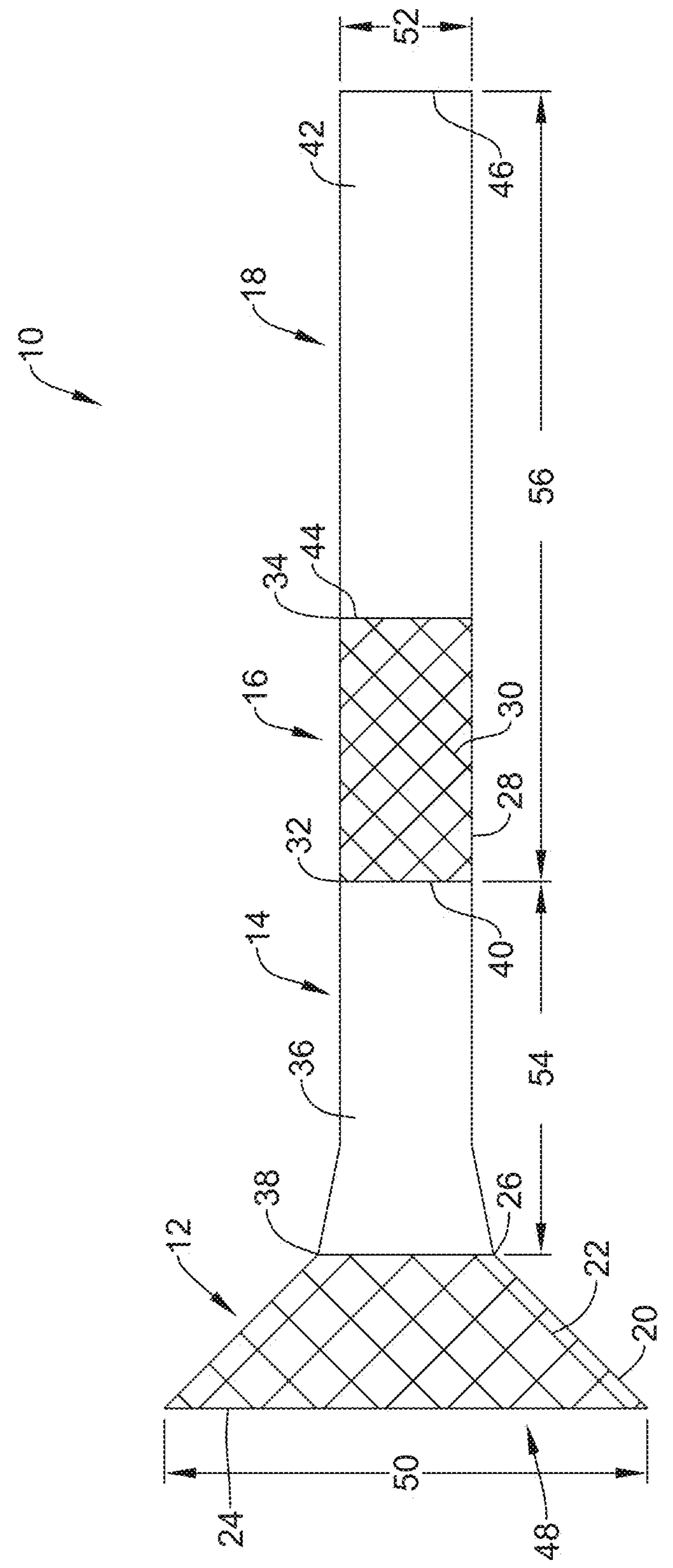
FIG. 1 is a side view of an illustrative implant.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

Gastric outlet obstruction (GOO) is the clinical and pathophysiological consequence of any disease process that produces a mechanical impediment to gastric emptying. The presence of GOO can be classified into disease conditions that affect the antrum and pylorus that lead to pyloric dysfunction or disease conditions of the proximal duodenum that restrict efferent flow. Clinical conditions such as peptic ulcer disease (PUD), pyloric stenosis, and gastric polyps represent etiologies for the former with pancreatic carcinoma, ampullary cancer, duodenal cancer, cholangiocarcinomas representing etiologies for the latter. In some instances, GOO may be directly treated through stenting the location using gastrointestinal (GI) self-expanding stents. However, placing a stent across the pyloric valve may leave the pylorus in a continually open position. However, this may result in gastric leakage into the duodenum. Alternative stent designs are desired to allow the immediate blockage to be opened while allowing for natural pyloric function to be retained.

FIG. 1 illustrates a side view of an illustrative endoluminal implant 10 including a plurality of regions, including, a first or proximal region 12, a second or intermediate region 14, a third or intermediate region 16, and a fourth or distal region 18. While the illustrative implant 10 is shown and described as having four regions 12, 14, 16, 18, it is contemplated the implant 10 may include any number of regions desired, such as, but not limited to, one, two, three, four, or more. Further, the regions 12, 14, 16, 18 may be any combination of structures and materials desired. In some cases, the implant 10 may include features (e.g., anti-migration flares, fixation spikes, sutures, etc.) to prevent distal/proximal displacement and/or migration of the implant 10, once the implant 10 is positioned and expanded in the body lumen. The implant 10 may include a lumen 48 extending entirely through the length of the implant 10, such as from a proximal end 24 of the first region 12 to a distal end 46 of the fourth region 18.

In some cases, the first region 12 may take the form of a stent 20 including an elongated tubular stent frame 22 defining a lumen. The stent 20 may be may be entirely, substantially, or partially covered with a polymeric covering, such as a coating (not explicitly shown). The covering may be disposed on an inner surface and/or outer surface of the stent 20, as desired. When so provided a polymeric covering may reduce or eliminate tissue ingrowth and/or reduce food impaction through interstices of the stent 20 into the lumen. It is contemplated that leaving an outer rim or a portion of the surface uncovered, an area of hyperplasia can be generated which would create a seal. The stent 20 may include regions of differing diameters. For example, the stent 20 may include a flared (e.g., enlarged relative to other portions of the stent 20) proximal end region 24 tapering radially inward to a distal end region. While not explicitly shown, the stent 20 may include regions of constant diameter or increasing diameters (e.g., in the distal direction), if so desired. The stent frame 22 may be expandable between a radially collapsed delivery configuration and a radially expanded deployed configuration. The expanded configuration may secure the implant 10 at the desired location in a body lumen.

In some cases, the third region 16 may take the form of a stent 28 including an elongated tubular stent frame 30 defining a lumen. The stent 28 may be may be entirely, substantially or partially, covered with a polymeric covering, such as a coating (not explicitly shown). The covering may be disposed on an inner surface and/or outer surface of the stent 28, as desired. When so provided a polymeric covering may reduce or eliminate tissue ingrowth and/or reduce food impaction through interstices of the stent 28 into the lumen. The stent 28 may have a uniform outer diameter from its proximal end region 32 to its distal end region 34. However, the stent 28 may include regions of differing diameters if so desired. The stent frame 30 may be expandable between a radially collapsed delivery configuration and a radially expanded deployed configuration. The expanded configuration may secure the implant 10 at the desired location in a body lumen. While not explicitly shown, in some embodiments, the distal stent 28 may extend distally to a distal end of the implant 10. Some additional but non-limiting alternative configurations are shown and described with respect to FIGS. 2-5.

The stent frames 22, 30 may have a woven structure, fabricated from a number of filaments. In some embodiments, the stent frames 22, 30 may be knitted with one filament, as is found, for example, in the ULTRAFLEX™ stents, made and distributed by Boston Scientific Corp. In other embodiments, the stent frames 22, 30 may be braided with several filaments, as is found, for example, in the WALLFLEX®, WALLSTENT®, and POLYFLEX® stents, made and distributed by Boston Scientific Corp. In yet another embodiment, the stent frames 22, 30 may be of a knotted type, such the PRECISION COLONIC™ stents made by Boston Scientific Corp. In still another embodiment, the stent frames 22, 30 may be laser cut, such as the EPIC™ stents made by Boston Scientific Corp. It is contemplated that the stent frames 22, 30 may be formed having the same structure as one another or having a different structure from one another.

It is contemplated that the stent frames 22, 30 can be made from a number of different materials such as, but not limited to, metals, metal alloys, shape memory alloys and/or polymers, as desired, enabling the stents 20, 28 to be expanded into shape when accurately positioned within the body. The material of the stent frames 22, 30 may be the same or different, as desired. In some instances, the material may be selected to enable the stents 20, 28 to be removed with relative ease as well. For example, the stent frames 22, 30 can be formed from alloys such as, but not limited to, nitinol and ELGILOY®. Depending the on material selected for construction, the stents 20, 28 may be self-expanding (i.e., configured to automatically radially expand when unconstrained). In some embodiments, fibers may be used to make the stent frames 22, 30, which may be composite fibers, for example, having an outer shell made of nitinol having a platinum core. It is further contemplated the stent frames 22, 30 may be formed from polymers including, but not limited to, polyethylene terephthalate (PET). In some embodiments, the stents 20, 28 may be self-expanding while in other embodiments, the stents 20, 28 may be expanded by an expansion device (such as, but not limited to a balloon inserted within a lumen 48 of the implant 10). As used herein the term "self-expanding" refers to the tendency of the stent to return to a preprogrammed diameter when unrestrained from an external biasing force (for example, but not limited to a delivery catheter or sheath).

One or both of the stents 20, 28 may include a one-way valve, such as an elastomeric slit valve or duck bill valve, positioned within the lumen 48 thereof to prevent retrograde flow of fluid or other material, such as gastrointestinal fluids.

In some cases, the second portion 14 may take the form of a proximal flexible sleeve 36 and the fourth portion 18 may take the form of a distal flexible sleeve 42. The proximal sleeve 36 may extend between the distal end of the proximal stent 20 and the proximal end of the distal stent 28. For example, the proximal sleeve 36 may be connected, affixed, or secured to the distal end region 26 of the first or proximal stent 20 adjacent to a proximal end region 38 of the sleeve 36. The proximal sleeve 36 may also be connected, affixed, or secured to the proximal end region 32 of the second or distal stent 28 adjacent to a distal end region 40 of the proximal sleeve 36. In some cases, the proximal sleeve 36 may overlap a portion or all of the proximal stent 20 and/or a portion or all of the distal stent 28. In some instances, the proximal sleeve 36 may be devoid of any structural components tending to hold the lumen 48 through the sleeve 36 open, thus allowing the sleeve 36 to collapse inward upon itself when subjected to the force of the pyloric valve closing off the lumen 48. The distal sleeve 42 may be connected, affixed, or secured to the distal end region 44 of the second or distal stent 28 adjacent to a proximal end region 44 of the sleeve 42 and extend distally to a distal end region 46. In some cases, the distal sleeve 42 may overlap a portion or all of the distal stent 28. It is contemplated that the sleeve 36, 42 may be formed as individual flexible membranes or as a single unitary structure, as desired. In some embodiments, the sleeves 36, 42 may extend partially, substantially, or all of the length of the implant 10 and cover all other portions (exterior surface and/or interior surface) of the implant 10, including the stents 20, 28. Said differently, while the regions 12, 14, 16, 18 have been described as a stent 20, 28 or a sleeve 36, 42, each region may include one or both of a frame structure and flexible sleeve structure. The sleeves 36, 42 may be secured to one or both of the stents 20, 28 by an adhesive or other methods known in the art, including by not limited to thermal methods, mechanical methods, etc.

The sleeves 36, 42 may each have an elongated, tubular shape defining a lumen. The lumen of the stents 20, 28 and the flexible sleeves 36, 42 may be fluidly connected to form the lumen 48 of the implant 10. It is contemplated that one or more of the regions 12, 14, 16, 18 of the implant 10 may include more than one lumen, as desired. The sleeves 36, 42 may be a thin flexible membrane that readily collapses on itself. For example one or both of the sleeves may be configured to collapse upon itself under the applied radial force exerted by a natural valve or sphincter when the implant 10 is deployed in a body lumen having a natural valve or sphincter. However, one or both of the sleeves 36, 42 may be provided with a radial support to hold it in the expanded configuration. Some examples and discussion of illustrative supports may be found in Patent Application No. 62/419,707, filed on Nov. 9, 2016, titled DEPLOYABLE SLEEVES AND RELATED METHODS, the disclosure of which is incorporated herein by reference.

The sleeves 36, 42 may include one or more of the following polymer materials: polyethylene, polypropylene, polystyrene, polyester, biosorbable plastics (e.g., polylactic acid), polycarbonate, polyvinyl chloride, polyacrylate, acrylate, polysulfone, polyetheretherketone, thermoplastic elastomers, thermoset elastomers (e.g., silicone), poly-p-xylylene (parylene), fluoropolymers (e.g., polytetrafluoroethylene (PTFE), polyvinylidene fluoride (PVDF), poly(vinylidene fluoride-co-hexafluoropropylene) (PVDFHFP)), bioplastics (e.g., cellulose acetate). The sleeves 36, 42 may additionally or alternatively include one or more of: polyurethane and its copolymers, ethylene vinyl-acetate, polyethylene terephthalate (PET), polyolefins, cellulosics, polyamides, acrylonitrile butadiene styrene copolymers, styrene isoprene butadiene (SIBS) block copolymers, acrylics, poly(glycolide-lactide) copolymer, Tecothane, PEBAX, poly(γ-caprolactone), poly(γ-hydroxybutyrate), polydioxanone, poly(γ-ethyl glutamate), polyiminocarbonates, poly(ortho ester), and/or polyanhydrides. Blends of the above polymers may also be employed, such as, but not limited to ChronoFlex®, manufactured by AdvanSource Biomaterials, based in Wilmington, MA, a family of biodurable aromatic polycarbonate based thermoplastic urethanes.

In further detail, the implant 10 may be generally cylindrical in shape, although this is not required, substantially flexible, and sized appropriately for a convenient accommodation within the digestive tract. It is contemplated that various shapes, sizes and designs of the implant may be constructed depending on the size and geometry of the cavities where the implant 10 has to be placed. In various examples, the implant 10 may have a length between 3-12 inches, 3-6 inches, 0.5-20 feet (0.15-6.1 meters), between 3-5 feet (0.9-1.5 meters), or about 2-4 feet (0.6-1.2 meters). However, the implant 10 may have a length of less than 0.5 feet (0.15 meters) or greater than 20 feet (6.1 meters) in some instances.

In one illustrative example, the implant 10 may be sized to be positioned within the outlet of the stomach, extend across the pylorus and into the duodenum to treat, for example, gastric outlet obstruction. In such an example, the proximal stent 20 may be sized to prevent the implant 10 from migrating distally through the stomach outlet. For example, the proximal end region 24 of the proximal stent 20 may have an outer diameter 50 in the range of about 25 millimeters (mm) to about 50 mm. It is contemplated that the shape of the proximal stent 20 may be formed to match or generally conform to the shape of the stomach exit. The proximal sleeve 36 may be configured to extend across the pylorus and may have a length 54 in the range of about 6 mm to about 15 mm. The distal stent 28 and the distal sleeve 42 may be sized to be positioned within the duodenal bulb and duodenum, respectively, and may have an outer diameter 52 in the range of about 15 mm to about 25 mm. The distal stent 28 and the distal sleeve 42 may together have a length 56 in the range of about 60 mm to about 150 mm. When the distal stent 28 extends distally to a distal end of the implant 10, the distal stent 28 may have a length 56 in the range of about 60 mm to about 150 mm. This is just an example. It is contemplated that the proximal sleeve 36 and/or the distal sleeve 42 may be positioned across other valved or sphincter regions with the proximal and/or distal stents 20, 28 sized and shaped for the adjacent anatomy.

Once implanted in a patient, the stents 20, 28 may exert a radially outward force to help secure the implant 10 to the body lumen. The implant 10 may be positioned in the antrum-pyloric-duodenum, esophagus, the gastro-esophageal junction (GEJ) region (e.g., at or near the cardia with the sleeve 24 extending into the esophagus), or at or near the pylorus with the sleeve 24 extending through the stomach or other portions of the gastro-intestinal system. In one example, the implant 10 may be positioned such that the proximal stent 20 is positioned at the stomach outlet with the proximal sleeve 36 bridging the pylorus. The flared structure of the proximal stent 20 may use the stomach to anchor the implant 10 and act as an anti-migration mechanism for the implant 10. For example, the large outer diameter 50 of the proximal end 24 of the proximal stent 20 may engage the stomach outlet to prevent or limit movement of the implant 10. The distal stent 28 may be placed within the duodenal bulb and the distal sleeve 42 may extend into the duodenum. The proximal sleeve 36 may be coupled to both the proximal stent 20 and the distal stent 28 such that a relative position of each section is fixed.

In some instances, the function of the pyloric valve may not have been impacted or degraded by the disease state which has caused the gastric outlet obstruction. In such an instance, it may be desirable to open the obstruction while still allowing for normal function of the pyloric valve. As described above, the proximal sleeve 36 may be formed from a flexible material. In other words, the proximal sleeve 36 may be free from any structure configured to exert a radially outward force on the surrounding tissue and may collapse upon itself under the applied radial force exerted by the natural valve or sphincter. This may allow the pyloric valve to function in a natural manner (e.g., to open and close). The distal stent 28 may be positioned adjacent to the gastric outlet obstruction. The stent frame 30 of the distal stent 28 may be constructed with sufficient radial force (e.g., to exert a sufficient radially outward force) to open the obstruction caused by the disease state.

Figure 2:
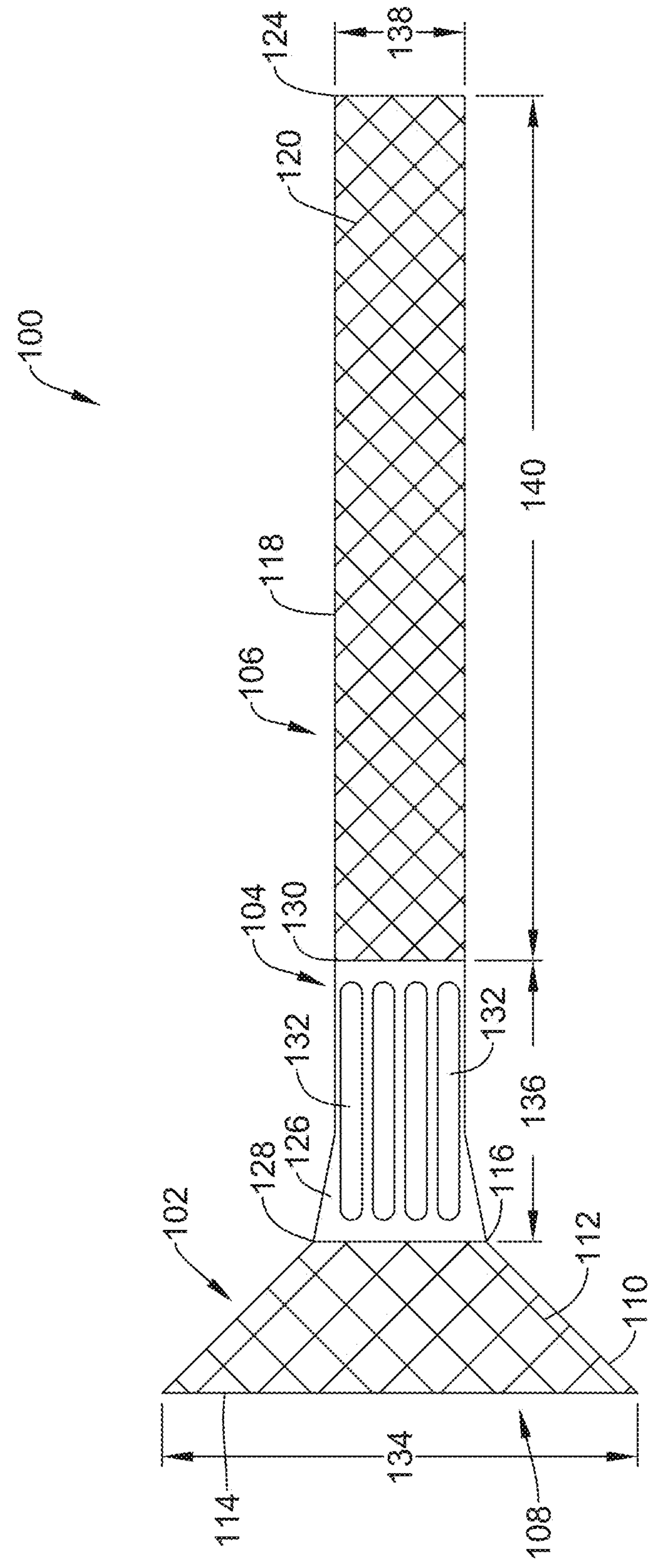
FIG. 2 is a side view of another illustrative implant.

FIG. 2 illustrates a side view of another illustrative implant 100 including a plurality of regions, including, a first or proximal region 102, a second or intermediate region 104, and a third or distal region 106. The illustrative implant 100 may be similar in form and function to the implant 10 described above. While the illustrative implant 100 is shown and described as having three regions 102, 104, 106, it is contemplated the implant 100 may include any number of regions desired, such as, but not limited to, one, two, three, four, or more. Further, the regions 102, 104, 106 may be any combination of structures and materials desired. In some cases, the implant 100 may include features (e.g., anti-migration flares, fixation spikes, sutures, etc.) to prevent distal/proximal displacement and/or migration of the implant 100, once the implant 100 is positioned and expanded in the body lumen. The implant 100 may include a lumen 108 extending from a proximal end 114 of the first region 102 to a distal end 124 of the third region 106.

In some cases, the first region 102 may take the form of a stent 110 including an elongated tubular stent frame 112 defining a lumen which may be similar in form and function to the proximal stent 20 described above. The stent 110 may be entirely, substantially or partially, covered with a polymeric covering, such as a coating (not explicitly shown). The covering may be disposed on an inner surface and/or outer surface of the stent frame 112, as desired. When so provided a polymeric covering may reduce or eliminate tissue ingrowth and/or reduce food impaction. The stent 110 may include regions of differing diameters. For example, the stent 110 may include a flared (e.g., enlarged relative to other portions of the stent 110) proximal end region 114 tapering radially inward in a distal direction to a distal end region 116. While not explicitly shown, the stent 110 may include regions of constant diameter or increasing diameters (e.g., increasing in the distal direction), if so desired. The stent frame 112 may be expandable between a radially collapsed delivery configuration and a radially expanded deployed configuration. The expanded configuration may secure the implant 100 at the desired location in a body lumen.

In some cases, the third region 106 may take the form of a stent 118 including an elongated tubular stent frame 120 defining a lumen which may be similar in form and function to the distal stent 28 described above. The stent 118 may be entirely, substantially or partially, covered with a polymeric covering, such as a coating (not explicitly shown). The covering may be disposed on an inner surface and/or outer surface of the stent frame 120, as desired. When so provided a polymeric covering may reduce or eliminate tissue ingrowth and/or reduce food impaction. The stent 118 may have a uniform outer diameter from its proximal end region 122 to its distal end region 124. However, the stent 118 may include regions of differing diameters if so desired. The stent frame 120 may be expandable between a radially collapsed delivery configuration and a radially expanded deployed configuration. The expanded configuration may secure the implant 100 at the desired location in a body lumen. While not explicitly shown, in some embodiments, the distal stent 118 may extend distally to a distal end of the implant 100.

In some cases, the second portion 104 may take the form of a flexible sleeve 126. The sleeve 126 may extend between the distal end of the proximal stent 110 and the proximal end of the distal stent 118. For example, the sleeve 126 may be connected, affixed, or secured to the distal end region 116 of the first or proximal stent 110 adjacent to a proximal end region 128 of the sleeve 126. The sleeve 126 may also be connected, affixed, or secured to the proximal end region 122 of the second or distal stent 118 adjacent to a distal end region 130 of the sleeve 126. In some cases, the sleeve 126 may overlap a portion or all of the proximal stent 110 and/or a portion or all of the distal stent 118. Said differently, the sleeve 126 may extend from the proximal end region 114 of the proximal stent 110 to the distal end region 124 of the distal stent 118 such that the implant 100 is fully covered. Alternatively, and/or additionally, one or both of the proximal stent 110 and the distal stent 118 may be covered with a material or structure different from the sleeve 126 to provide a fully covered implant 100. The sleeve 126 may be secured to one or both of the stents 110, 118 by an adhesive or other methods known in the art, including by not limited to thermal methods, mechanical methods, etc.

The sleeve 126 may have an elongated, tubular shape defining a lumen which may be similar in form or function to the sleeves 36, 42 described above. The lumen of the stents 110, 118 and the flexible sleeve 126 may be fluidly connected to form the lumen 108 of the implant 100. It is contemplated that one or more of the regions 102, 104, 106 of the implant 100 may include more than one lumen, as desired. The sleeve 126 may be a thin flexible membrane that readily collapses on itself. However, in some instances, the sleeve 126 may be provided with a radial support.

The sleeve 126 may include one or more longitudinally extending slots 132 extending through a thickness of the sleeve 126. The removal of material to form the slots 132 may allow for a connecting element to remain between the proximal stent 110 and the distal stent 118 while increasing the deformability and/or moveability of the sleeve 126. Thus, when the sleeve 126 is positioned across a valve or sphincter, such as, but not limited to the pyloric valve, the reduced amount of material placed across the valve region may further allow for normal valve function. The sleeve 126 may include any number of longitudinally extending slots 132 desired, such as, but not limited to one, two, three, four, or more. The slots 132 may be positioned uniformly about a circumference of the sleeve 126 (e.g., having a uniform distance between adjacent slots 132) or eccentrically about a circumference of the sleeve 126 (e.g., having an unequal distant between adjacent slots 132). While the slots 132 have been described as extending longitudinally (e.g., along a longitudinal axis of the implant 100), it is contemplated that the slots 132 may extend along non-parallel angles relative to the longitudinal axis of the implant 100. For example, the slots 132 may extend in a helical manner about a circumference of the sleeve 126.

In one illustrative example, the implant 100 may be sized to be positioned within the outlet of the stomach, extend across the pylorus and into the duodenum to treat, for example, gastric outlet obstruction. In such an example, the proximal stent 110 may be sized to prevent implant 100 from migrating distally through the stomach outlet. For example, the proximal end region 114 of the proximal stent 110 may have an outer diameter 134 in the range of about 25 millimeters (mm) to about 50 mm. It is contemplated that the shape of the proximal stent 110 may be formed to match or generally conform to the shape of the stomach exit. The sleeve 126 may be configured to extend across the pylorus and may have a length 136 in the range of about 6 mm to about 15 mm. The distal stent 118 may be sized to be positioned within the duodenal bulb and duodenum, respectively, and may have an outer diameter 138 in the range of about 15 mm to about 25 mm. The distal stent 118 may have a length 140 in the range of about 60 mm to about 150 mm. This is just an example. It is contemplated that the sleeve 126 may be positioned across other valved or sphincter regions with the proximal and/or distal stents 110, 118 sized and shaped for the adjacent anatomy.

Once implanted in a patient, the stents 110, 118 may exert a radially outward force to help secure the implant 100 to the body lumen. The implant 100 may be positioned in the esophagus, the gastro-esophageal junction (GEJ) region, or at or near the pylorus with the sleeve 114 extending through the stomach or other portions of the gastro-intestinal system. In one example, the implant 100 may be positioned such that the proximal stent 110 is positioned at the stomach outlet with the sleeve 126 bridging the pylorus. The flared structure of the proximal stent 110 may use the stomach to anchor the implant 100 and act as an anti-migration mechanism for the implant 100. For example, the large outer diameter 134 of the proximal end 114 of the proximal stent 110 may engage the stomach outlet to prevent or limit movement of the implant 100. The distal stent 118 may be placed within the duodenal bulb and may extend into the duodenum. The sleeve 126 may be coupled to both the proximal stent 110 and the distal stent 118 such that a relative position of each section is fixed.

In some instances, the function of the pyloric valve may not have been impacted or degraded by the disease state which has caused the gastric outlet obstruction. In such an instance, it may be desirable to open the obstruction while still allowing for normal function of the pyloric valve. As described above, the sleeve 126 may be formed from a flexible material which may be made more flexible or pliable through the addition of slots 132. In other words, the sleeve 126, and thus the length of the intermediate region 104 between the proximal stent 110 and the distal stent 118, may be free from any structure configured to exert a radially outward force on the surrounding tissue. This may allow the pyloric valve to function in a natural manner (e.g., to open and close). The distal stent 118 may be positioned adjacent to the gastric outlet obstruction. The stent frame 120 of the distal stent 118 may be constructed with sufficient radial force (e.g., to exert a sufficient radially outward force) to open the obstruction caused by the disease state.

Figure 3:
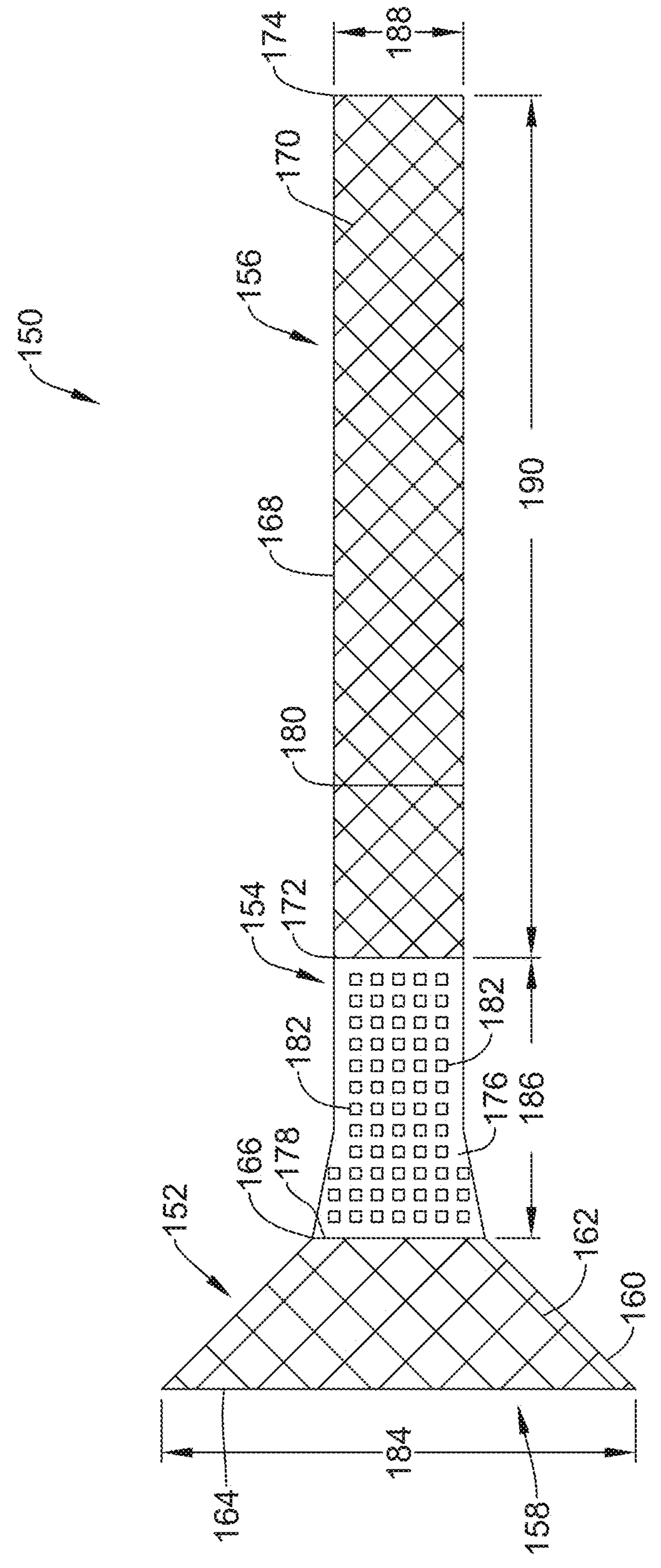
FIG. 3 is a side view of another illustrative implant.

FIG. 3 illustrates a side view of another illustrative implant 150 including a plurality of regions, including, a first region 152, a second region 154, and a third region 156. The illustrative implant 150 may be similar in form and function to the implant 10 described above. While the illustrative implant 150 is shown and described as having three regions 152, 154, 156, it is contemplated the implant 150 may include any number of regions desired, such as, but not limited to, one, two, three, four, or more. Further, the regions 152, 154, 156 may be any combination of structures and materials desired. In some cases, the implant 150 may include features (e.g., anti-migration flares, fixation spikes, sutures, etc.) to prevent distal/proximal displacement and/or migration of the implant 150, once the implant 150 is positioned and expanded in the body lumen. The implant 150 may include a lumen 158 extending from a proximal end 164 of the first region 152 to a distal end 174 of the third region 156.

In some cases, the first region 152 may take the form of a stent 160 including an elongated tubular stent frame 162 defining a lumen which may be similar in form and function to the proximal stent 20 described above. The stent 160 may be entirely, substantially or partially, covered with a polymeric covering, such as a coating (not explicitly shown). The covering may be disposed on an inner surface and/or outer surface of the stent frame 162, as desired. When so provided a polymeric covering may reduce or eliminate tissue ingrowth and/or reduce food impaction. The stent 160 may include regions of differing diameters. For example, the stent 160 may include a flared (e.g., enlarged relative to other portions of the stent 160) proximal end region 164 tapering radially inward in a distal direction to a distal end region 166. While not explicitly shown, the stent 160 may include regions of constant diameter or increasing diameters (e.g., increasing in the distal direction), if so desired. The stent frame 162 may be expandable between a radially collapsed delivery configuration and a radially expanded deployed configuration. The expanded configuration may secure the implant 150 at the desired location in a body lumen.

In some cases, the third region 156 may take the form of a stent 168 including an elongated tubular stent frame 170 defining a lumen which may be similar in form and function to the distal stent 28 described above. The stent 168 may be entirely, substantially or partially, covered with a polymeric covering, such as a coating (not explicitly shown). For example, a partial covering could be used to cause hyperplasia for fixation or, for example, for biliary, or other, access. The covering may be disposed on an inner surface and/or outer surface of the stent frame 170, as desired. When so provided a polymeric covering may reduce or eliminate tissue ingrowth and/or reduce food impaction. The stent 168 may have a uniform outer diameter from its proximal end region 172 to its distal end region 174. However, the stent 168 may include regions of differing diameters if so desired. The stent frame 170 may be expandable between a radially collapsed delivery configuration and a radially expanded deployed configuration. The expanded configuration may secure the implant 150 at the desired location in a body lumen. While not explicitly shown, in some embodiments, the distal stent 168 may extend distally to a distal end of the implant 150.

In some cases, the second portion 154 may take the form of a flexible sleeve 176. The sleeve 176 may extend between the distal end of the proximal stent 160 and the proximal end of the distal stent 168. For example, the sleeve 176 may be connected, affixed, or secured to the distal end region 166 of the first or proximal stent 160 adjacent to a proximal end region 178 of the sleeve 176. The sleeve 176 may also be connected, affixed, or secured adjacent or distal to the proximal end region 172 of the second or distal stent 168 adjacent to a distal end region 180 of the sleeve 176. In some cases, the sleeve 176 may overlap a portion or all of the proximal stent 160 and/or a portion of the distal stent 168. Said differently, the sleeve 176 may extend from the proximal end region 164 of the proximal stent 160 to a location proximal to the distal end region 174 of the distal stent 168 such that the implant 150 is not fully covered. For example, at least a portion of the distal stent 168 may be a bare stent. This may allow for tissue ingrowth to further secure the implant 150. In some instances, all or a portion of the proximal stent 160 may be bare. Alternatively, and/or additionally, one or both of the proximal stent 160 and the distal stent 168 may be covered with a material or structure different from the sleeve 176 to provide a partially covered implant 150. The sleeve 176 may be secured to one or both of the stents 160, 168 by an adhesive or other methods known in the art, including by not limited to thermal methods, mechanical methods, etc.

The sleeve 176 may have an elongated, tubular shape defining a lumen which may be similar in form or function to the sleeves 36, 42 described above. The lumen of the stents 160, 168 and the flexible sleeve 176 may be fluidly connected to form the lumen 158 of the implant 150. It is contemplated that one or more of the regions 152, 154, 156 of the implant 150 may include more than one lumen, as desired. The sleeve 176 may be a thin flexible membrane that readily collapses on itself. However, in some instances, the sleeve 176 may be provided with a radial support.

The sleeve 176 may include one or more apertures 182 extending through a thickness of the sleeve 176. For example, the sleeve 176 may have a mesh-like structure. The removal of material to form the apertures 182 may allow for a connecting element to remain between the proximal stent 160 and the distal stent 168 while increasing the deformability and/or moveability of the sleeve 176. Thus, when the sleeve 176 is positioned across a valve or sphincter, such as, but not limited to the pyloric valve, the reduced amount of material placed across the valve region may further allow for normal valve function. The sleeve 176 may include any number of apertures 182 desired, such as, but not limited to one, two, three, ten, twenty, fifty, or more. The apertures 182 may be positioned uniformly about a circumference and/or length of the sleeve 176 (e.g., having a uniform distance between adjacent apertures 182) or eccentrically about a circumference and/or length of the sleeve 176 (e.g., having an unequal distant between adjacent apertures 182).

In one illustrative example, the implant 150 may be sized to be positioned within the outlet of the stomach, extend across the pylorus and into the duodenum to treat, for example, gastric outlet obstruction. In such an example, the proximal stent 160 may be sized to prevent implant 150 from migrating distally through the stomach outlet. For example, the proximal end region 164 of the proximal stent 160 may have an outer diameter 184 in the range of about 25 millimeters (mm) to about 50 mm. It is contemplated that the shape of the proximal stent 160 may be formed to match or generally conform to the shape of the stomach exit. The sleeve 176 may be configured to extend across the pylorus and may have a length 186 in the range of about 6 mm to about 15 mm. The distal stent 168 may be sized to be positioned within the duodenal bulb and duodenum, respectively, and may have an outer diameter 188 in the range of about 15 mm to about 25 mm. The distal stent 168 may have a length 190 in the range of about 60 mm to about 150 mm. This is just an example. It is contemplated that the sleeve 176 may be positioned across other valved or sphincter regions with the proximal and/or distal stents 160, 168 sized and shaped for the adjacent anatomy.

Once implanted in a patient, the stents 160, 168 may exert a radially outward force to help secure the implant 150 to the body lumen. The implant 150 may be positioned in the esophagus, the gastro-esophageal junction (GEJ) region, or at or near the pylorus with the sleeve 164 extending through the stomach or other portions of the gastro-intestinal system. In one example, the implant 150 may be positioned such that the proximal stent 160 is positioned at the stomach outlet with the sleeve 176 bridging the pylorus. The flared structure of the proximal stent 160 may use the stomach to anchor the implant 150 and act as an anti-migration mechanism for the implant 150. For example, the large outer diameter 184 of the proximal end 164 of the proximal stent 160 may engage the stomach outlet to prevent or limit movement of the implant 150. The distal stent 168 may be placed within the duodenal bulb and may extend into the duodenum. The sleeve 176 may be coupled to both the proximal stent 160 and the distal stent 168 such that a relative position of each section is fixed.

In some instances, the function of the pyloric valve may not have been impacted or degraded by the disease state which has caused the gastric outlet obstruction. In such an instance, it may be desirable to open the obstruction while still allowing for normal function of the pyloric valve. As described above, the sleeve 176 may be formed from a flexible material which may be made more flexible or pliable through the addition of apertures 182. In other words, the sleeve 176, and thus the length of the intermediate region 154 between the proximal stent 160 and the distal stent 168, may be free from any structure configured to exert a radially outward force on the surrounding tissue. This may allow the pyloric valve to function in a natural manner (e.g., to open and close). The distal stent 168 may be positioned adjacent to the gastric outlet obstruction. The stent frame 170 of the distal stent 168 may be constructed with sufficient radial force (e.g., to exert a sufficient radially outward force) to open the obstruction caused by the disease state.

Figure 4:
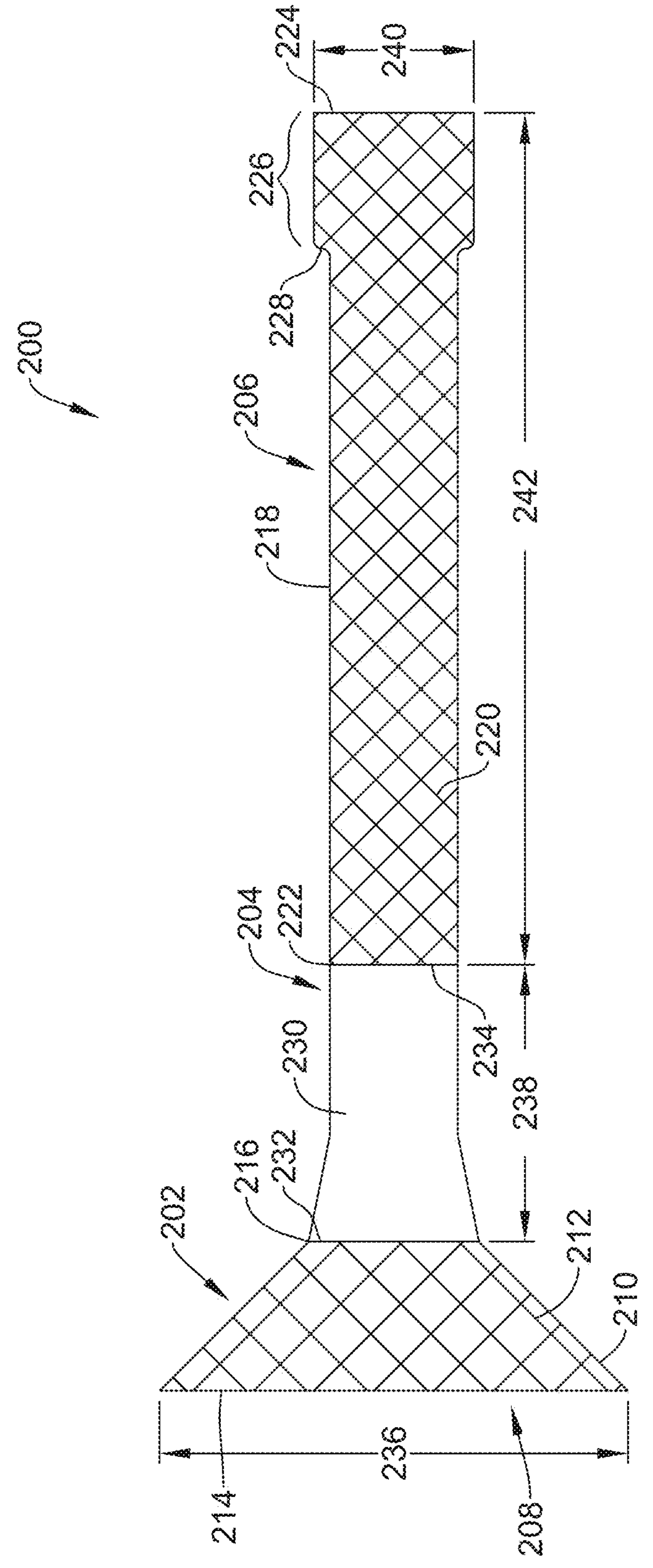
FIG. 4 is a side view of another illustrative implant.

FIG. 4 illustrates a side view of another illustrative implant 200 including a plurality of regions, including, a first region 202, a second region 204, and a third region 206. The illustrative implant 200 may be similar in form and function to the implant 10 described above. While the illustrative implant 200 is shown and described as having three regions 202, 204, 206, it is contemplated the implant 200 may include any number of regions desired, such as, but not limited to, one, two, three, four, or more. Further, the regions 202, 204, 206 may be any combination of structures and materials desired. In some cases, the implant 200 may include features (e.g., anti-migration flares, fixation spikes, sutures, etc.) to prevent distal/proximal displacement and/or migration of the implant 200, once the implant 200 is positioned and expanded in the body lumen. The implant 200 may include a lumen 208 extending from a proximal end 214 of the first region 202 to a distal end 224 of the third region 206.

In some cases, the first region 202 may take the form of a stent 210 including an elongated tubular stent frame 212 defining a lumen which may be similar in form and function to the proximal stent 20 described above. The stent 210 may be entirely, substantially or partially, covered with a polymeric covering, such as a coating (not explicitly shown). The covering may be disposed on an inner surface and/or outer surface of the stent frame 212, as desired. When so provided a polymeric covering may reduce or eliminate tissue ingrowth and/or reduce food impaction. The stent 210 may include regions of differing diameters. For example, the stent 210 may include a flared (e.g., enlarged relative to other portions of the stent 210) proximal end region 214 tapering radially inward in a distal direction to a distal end region 216. While not explicitly shown, the stent 210 may include regions of constant diameter or increasing diameters (e.g., increasing in the distal direction), if so desired. The stent frame 212 may be expandable between a radially collapsed delivery configuration and a radially expanded deployed configuration. The expanded configuration may secure the implant 200 at the desired location in a body lumen.

In some cases, the third region 206 may take the form of a stent 218 including an elongated tubular stent frame 220 defining a lumen which may be similar in form and function to the distal stent 28 described above. The stent 218 may be entirely, substantially or partially, covered with a polymeric covering, such as a coating (not explicitly shown). The covering may be disposed on an inner surface and/or outer surface of the stent frame 220, as desired. When so provided a polymeric covering may reduce or eliminate tissue ingrowth and/or reduce food impaction. The stent 218 may have a uniform outer diameter from its proximal end region 222 to a location proximal to its distal end region 224. In some instances, the distal end region 224 may include a flared region 226 (e.g., increasing in diameter or having an enlarged diameter relative to other portions of the stent 218). In some embodiments, the flared region 226 may include a transition region 228 which may be abrupt or step-wise or flared or sloped, as desired to a relatively constant enlarged diameter. In other embodiments, the flared region may slope or flare along its entire length (e.g., a continuously changing outer diameter). The stent frame 220 may be expandable between a radially collapsed delivery configuration and a radially expanded deployed configuration. The expanded configuration may secure the implant 200 at the desired location in a body lumen. While not explicitly shown, in some embodiments, the distal stent 218 may extend distally to a distal end of the implant 200.

In some cases, the second portion 204 may take the form of a flexible sleeve 230. The sleeve 230 may extend between the distal end of the proximal stent 210 and the proximal end of the distal stent 218. For example, the sleeve 230 may be connected, affixed, or secured to the distal end region 216 of the first or proximal stent 210 adjacent to a proximal end region 232 of the sleeve 230. The sleeve 230 may also be connected, affixed, or secured adjacent or distal to the proximal end region 222 of the second or distal stent 218 adjacent to a distal end region 234 of the sleeve 230. In some cases, the sleeve 230 may overlap a portion or all of the proximal stent 210 and/or a portion of the distal stent 218. Said differently, the sleeve 230 may extend from the proximal end region 214 of the proximal stent 210 to the distal end region 224 of the distal stent 218 such that the implant 200 is fully covered. Alternatively, and/or additionally, one or both of the proximal stent 210 and the distal stent 218 may be covered with a material or structure different from the sleeve 230 to provide a partially covered implant 200. The sleeve 230 may be secured to one or both of the stents 210, 218 by an adhesive or other methods known in the art, including by not limited to thermal methods, mechanical methods, etc.

The sleeve 230 may have an elongated, tubular shape defining a lumen which may be similar in form or function to the sleeves 36, 42 described above. The lumen of the stents 210, 218 and the flexible sleeve 230 may be fluidly connected to form the lumen 208 of the implant 200. It is contemplated that one or more of the regions 202, 204, 206 of the implant 200 may include more than one lumen, as desired. The sleeve 230 may be a thin flexible membrane that readily collapses on itself. However, in some instances, the sleeve 230 may be provided with a radial support.

In one illustrative example, the implant 200 may be sized to be positioned within the outlet of the stomach, extend across the pylorus and into the duodenum to treat, for example, gastric outlet obstruction. In such an example, the proximal stent 210 may be sized to prevent implant 200 from migrating distally through the stomach outlet. For example, the proximal end region 214 of the proximal stent 210 may have an outer diameter 236 in the range of about 25 millimeters (mm) to about 50 mm. It is contemplated that the shape of the proximal stent 210 may be formed to match or generally conform to the shape of the stomach exit. The sleeve 230 may be configured to extend across the pylorus and may have a length 238 in the range of about 6 mm to about 15 mm. The distal stent 218 may be sized to be positioned within the duodenal bulb and duodenum, respectively, and may have an outer diameter 240 in the range of about 15 mm to about 25 mm. The distal stent 218 may have a length 242 in the range of about 60 mm to about 200 mm. This is just an example. It is contemplated that the sleeve 230 may be positioned across other valved or sphincter regions with the proximal and/or distal stents 210, 218 sized and shaped for the adjacent anatomy.

Once implanted in a patient, the stents 210, 218 may exert a radially outward force to help secure the implant 200 to the body lumen. The implant 200 may be positioned in the esophagus, the gastro-esophageal junction (GEJ) region, or at or near the pylorus with the sleeve 214 extending through the stomach or other portions of the gastro-intestinal system. In one example, the implant 200 may be positioned such that the proximal stent 210 is positioned at the stomach outlet with the sleeve 230 bridging the pylorus. The flared structure of the proximal stent 210 may use the stomach to anchor the implant 200 and act as an anti-migration mechanism for the implant 200. For example, the large outer diameter 236 of the proximal end 214 of the proximal stent 210 may engage the stomach outlet to prevent or limit movement of the implant 200. The distal stent 218 may be placed within the duodenal bulb and may extend into the duodenum. The sleeve 230 may be coupled to both the proximal stent 210 and the distal stent 218 such that a relative position of each section is fixed.

In some instances, the function of the pyloric valve may not have been impacted or degraded by the disease state which has caused the gastric outlet obstruction. In such an instance, it may be desirable to open the obstruction while still allowing for normal function of the pyloric valve. In other words, the sleeve 230, and thus the length of the intermediate region 204 between the proximal stent 210 and the distal stent 218, may be free from any structure configured to exert a radially outward force on the surrounding tissue. This may allow the pyloric valve to function in a natural manner (e.g., to open and close). The distal stent 218 may be positioned adjacent to the gastric outlet obstruction. The stent frame 220 of the distal stent 218 may be constructed with sufficient radial force (e.g., to exert a sufficient radially outward force) to open the obstruction caused by the disease state.

Figure 5:
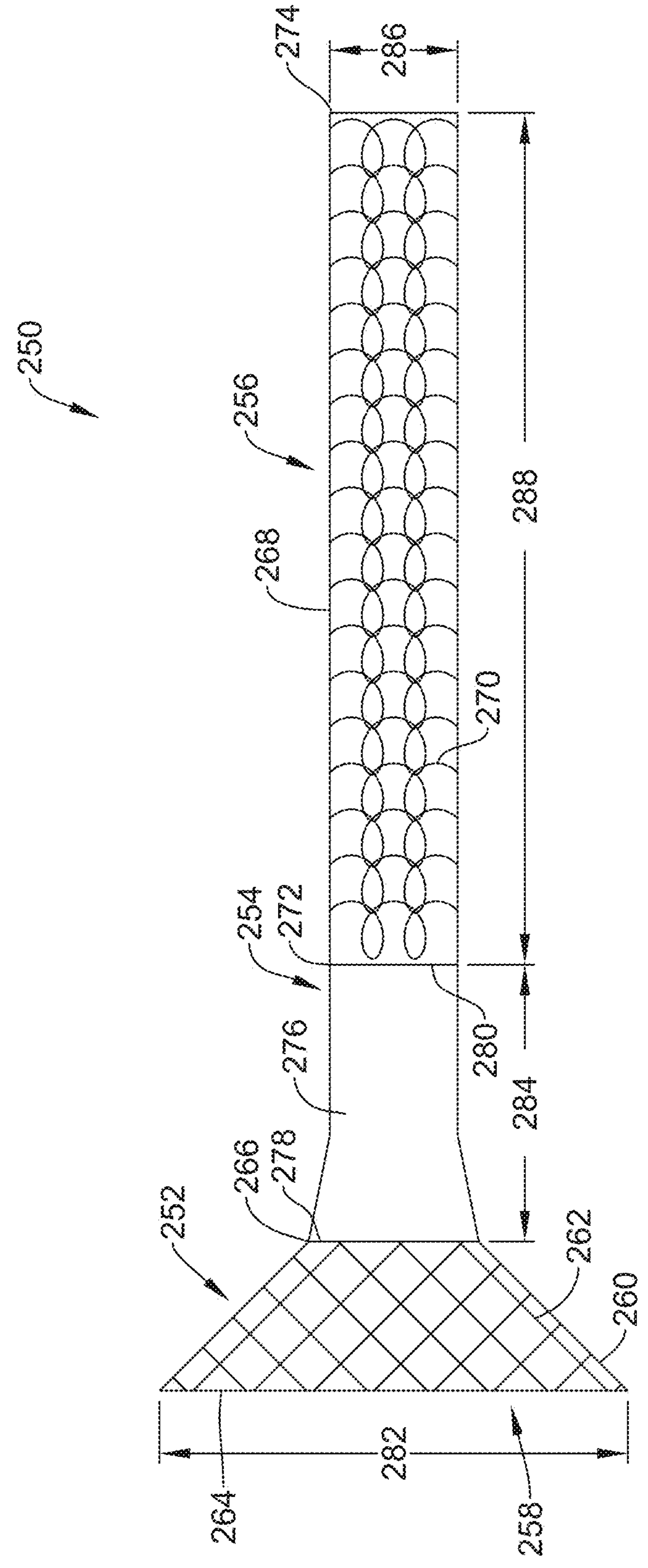
FIG. 5 is a side view of another illustrative implant.

FIG. 5 illustrates a side view of another illustrative implant 250 including a plurality of regions, including, a first region 252, a second region 254, and a third region 256. The illustrative implant 250 may be similar in form and function to the implant 10 described above. While the illustrative implant 250 is shown and described as having three regions 252, 254, 256, it is contemplated the implant 250 may include any number of regions desired, such as, but not limited to, one, two, three, four, or more. Further, the regions 252, 254, 256 may be any combination of structures and materials desired. In some cases, the implant 250 may include features (e.g., anti-migration flares, fixation spikes, sutures, etc.) to prevent distal/proximal displacement and/or migration of the implant 250, once the implant 250 is positioned and expanded in the body lumen. The implant 250 may include a lumen 258 extending from a proximal end 264 of the first region 252 to a distal end 224 of the third region 256.

In some cases, the first region 252 may take the form of a stent 260 including an elongated tubular stent frame 262 defining a lumen which may be similar in form and function to the proximal stent 20 described above. The stent 260 may be entirely, substantially or partially, covered with a polymeric covering, such as a coating (not explicitly shown). The covering may be disposed on an inner surface and/or outer surface of the stent frame 262, as desired. When so provided a polymeric covering may reduce or eliminate tissue ingrowth and/or reduce food impaction. The stent 260 may include regions of differing diameters. For example, the stent 260 may include a flared (e.g., enlarged relative to other portions of the stent 260) proximal end region 264 tapering radially inward in a distal direction to a distal end region 266. While not explicitly shown, the stent 260 may include regions of constant diameter or increasing diameters (e.g., increasing in the distal direction), if so desired. The stent frame 262 may be expandable between a radially collapsed delivery configuration and a radially expanded deployed configuration. The expanded configuration may secure the implant 250 at the desired location in a body lumen.

In some cases, the third region 256 may take the form of a stent 268 including an elongated tubular stent frame 270 defining a lumen which may be similar in form and function to the distal stent 28 described above. In some embodiments, the distal stent frame 270 may be formed using a different technique from the proximal stent frame 262. For example, the distal stent frame 270 may be knitted while the proximal stent frame 262 may be braided. This is just an example. Other combinations of stent frames may be used, as desired. The stent 268 may be entirely, substantially or partially, covered with a polymeric covering, such as a coating (not explicitly shown). The covering may be disposed on an inner surface and/or outer surface of the stent frame 270, as desired. When so provided a polymeric covering may reduce or eliminate tissue ingrowth and/or reduce food impaction. The stent 268 may have a uniform outer diameter from its proximal end region 272 to its distal end region 274. However, the stent 268 may include regions of differing diameters if so desired. The stent frame 270 may be expandable between a radially collapsed delivery configuration and a radially expanded deployed configuration. The expanded configuration may secure the implant 250 at the desired location in a body lumen. While not explicitly shown, in some embodiments, the distal stent 268 may extend distally to a distal end of the implant 250.

In some cases, the second portion 254 may take the form of a flexible sleeve 276. The sleeve 276 may extend between the distal end of the proximal stent 260 and the proximal end of the distal stent 268. For example, the sleeve 276 may be connected, affixed, or secured to the distal end region 266 of the first or proximal stent 260 adjacent to a proximal end region 278 of the sleeve 276. The sleeve 276 may also be connected, affixed, or secured adjacent or distal to the proximal end region 222 of the second or distal stent 268 adjacent to a distal end region 280 of the sleeve 276. In some cases, the sleeve 276 may overlap a portion or all of the proximal stent 260 and/or a portion of the distal stent 268. Said differently, the sleeve 276 may extend from the proximal end region 264 of the proximal stent 260 to the distal end region 224 of the distal stent 268 such that the implant 250 is fully covered. Alternatively, and/or additionally, one or both of the proximal stent 260 and the distal stent 268 may be covered with a material or structure different from the sleeve 276 to provide a partially covered implant 250. The sleeve 276 may be secured to one or both of the stents 260, 268 by an adhesive or other methods known in the art, including by not limited to thermal methods, mechanical methods, etc.

The sleeve 276 may have an elongated, tubular shape defining a lumen which may be similar in form or function to the sleeves 36, 42 described above. The lumen of the stents 260, 268 and the flexible sleeve 276 may be fluidly connected to form the lumen 258 of the implant 250. It is contemplated that one or more of the regions 252, 254, 256 of the implant 250 may include more than one lumen, as desired. The sleeve 276 may be a thin flexible membrane that readily collapses on itself. However, in some instances, the sleeve 276 may be provided with a radial support.

In one illustrative example, the implant 250 may be sized to be positioned within the outlet of the stomach, extend across the pylorus and into the duodenum to treat, for example, gastric outlet obstruction. In such an example, the proximal stent 260 may be sized to prevent implant 250 from migrating distally through the stomach outlet. For example, the proximal end region 264 of the proximal stent 260 may have an outer diameter 282 in the range of about 25 millimeters (mm) to about 50 mm. It is contemplated that the shape of the proximal stent 260 may be formed to match or generally conform to the shape of the stomach exit. The sleeve 276 may be configured to extend across the pylorus and may have a length 284 in the range of about 6 mm to about 15 mm. The distal stent 268 may be sized to be positioned within the duodenal bulb and duodenum, respectively, and may have an outer diameter 286 in the range of about 15 mm to about 25 mm. The distal stent 268 may have a length 288 in the range of about 60 mm to about 250 mm. This is just an example. It is contemplated that the sleeve 276 may be positioned across other valved or sphincter regions with the proximal and/or distal stents 260, 268 sized and shaped for the adjacent anatomy.

Once implanted in a patient, the stents 260, 268 may exert a radially outward force to help secure the implant 250 to the body lumen. The implant 250 may be positioned in the esophagus, the gastro-esophageal junction (GEJ) region, or at or near the pylorus with the sleeve 264 extending through the stomach or other portions of the gastro-intestinal system. In one example, the implant 250 may be positioned such that the proximal stent 260 is positioned at the stomach outlet with the sleeve 276 bridging the pylorus. The flared structure of the proximal stent 260 may use the stomach to anchor the implant 250 and act as an anti-migration mechanism for the implant 250. For example, the large outer diameter 282 of the proximal end 264 of the proximal stent 260 may engage the stomach outlet to prevent or limit movement of the implant 250. The distal stent 268 may be placed within the duodenal bulb and may extend into the duodenum. The sleeve 276 may be coupled to both the proximal stent 260 and the distal stent 268 such that a relative position of each section is fixed.

In some instances, the function of the pyloric valve may not have been impacted or degraded by the disease state which has caused the gastric outlet obstruction. In such an instance, it may be desirable to open the obstruction while still allowing for normal function of the pyloric valve. In other words, the sleeve 276, and thus the length of the intermediate region 254 between the proximal stent 260 and the distal stent 268, may be free from any structure configured to exert a radially outward force on the surrounding tissue. This may allow the pyloric valve to function in a natural manner (e.g., to open and close). The distal stent 268 may be positioned adjacent to the gastric outlet obstruction. The stent frame 270 of the distal stent 268 may be constructed with sufficient radial force (e.g., to exert a sufficient radially outward force) to open the obstruction caused by the disease state.

Figure 6:
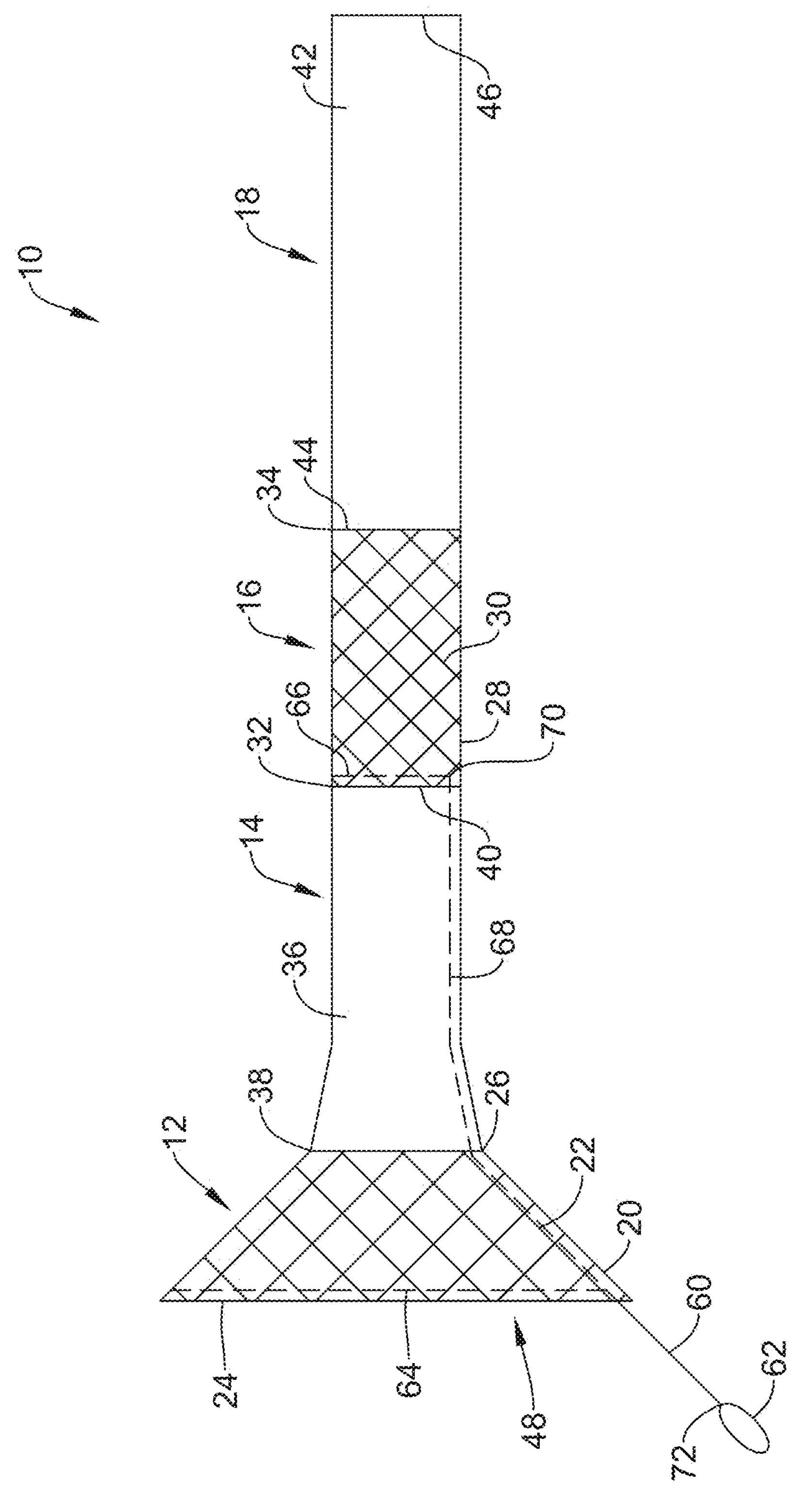
FIG. 6 is a side view of the illustrative implant of FIG. 1 with a retrieval suture in a first configuration.

FIG. 6 illustrates a side view of the illustrative implant 10 of FIG. 1 including a retrieval suture 60. Some implants, such as, but not limited to the implant 10 shown in FIG. 6 may be designed or intended to be removable or repositionable. In some cases, a suture, such as, but not limited to, the suture 60 illustrated may be used to collapse a portion of the implant (in some instances, the suture may be woven through the scaffolding adjacent a proximal end of the implant) to reduce the profile of an implant. As described above, the implant 10 may be positioned across a valve location (e.g., the pyloric valve) such that the proximal stent 20 is proximal to the valve and the distal stent 28 is distal to the valve. As the stent frame 22 of the proximal stent 20 is not directly coupled with the stent frame 30 of the distal stent 28, a suture woven through the proximal end region 24 of the proximal stent 20 may not necessarily reduce the profile of both the proximal stent 20 and the distal stent 28. It is contemplated that in order to remove or reposition the implant 10 both the profile of the proximal stent 20 and the distal stent 28 may need to be reduced in order to move the implant 10. For example, the distal stent 28 may have a deployed diameter that is larger than the pyloric valve (or other natural valve) to prevent or reduce proximal migration. As such, to move the implant 10 a profile of the distal stent 28 may need to be reduced from its deployed configuration.

In order to collapse both the proximal stent 20 and the distal stent 28, the suture 60 may include a plurality of components or regions each configured to perform a function. A first region of the suture 60 may be a retrieval suture loop 62 which may be configured to be grasped by forceps or another tool during a clinical procedure for stent removal or repositioning. The retrieval suture loop 62 may extend proximally from the proximal end region 24 of the proximal stent 20 to allow the retrieval suture loop 62 to be easily grasped and pulled in a proximal direction. However, this is not required. In some instances, it may be desirable to position the retrieval suture loop 62 near the distal stent 28. It is contemplated that the suture 60 may be arranged in a number of different patterns such that various portions of the proximal stent 20 and/or the distal stent 28 are collapsed in a desired order. For example, in some instances, it may be desirable to collapse the proximal end region 32 of the distal stent 28 prior to collapsing the proximal stent 20.

A second region of the suture 60 may include a first suture loop 64 which is interwoven to the proximal end region 24 of the proximal stent 20. The first suture loop 64 may extend around the entire circumference of the proximal end region 24 of the proximal stent 20. The first suture loop 64 may be configured to reduce a profile of the proximal stent 20 from its deployed configuration. A third region of the suture 60 may include a second suture loop 66 which is interwoven through the proximal end region 32 of the distal stent 28. The second suture loop 66 may extend around the entire circumference of the proximal end region 32 of the distal stent 28. The second suture loop 66 may be configured to reduce the profile of the distal stent 28 from its deployed configuration. A fourth region of the suture 60 may include a connecting suture portion 68 that extends between and couples the first suture loop 64 and the second suture loop 66. The connecting suture portion 68 may be configured to couple the first suture loop 64 and the second suture loop 66 such that actuation of the retrieval suture loop 62 is translated to both the first suture loop 64 and the second suture loop 66. It is noted that in some instances, the suture 60 may not include a portion, such as the retrieval suture loop 62, extending proximally from the first suture loop 64, and thus surgical personnel may grasp the first suture loop 64 directly to initiate retrieval of the implant 10.

The suture 60 may be formed from a length of material having a first end 70 and a second end 72. The length of material may be one long continuous unitary structure or a plurality of structures coupled together, as desired. To assemble the suture 60 with the implant 10, the first end 70 may be interwoven through the stent frame 22 adjacent the proximal end region 24 of the proximal stent 20 until it extends about the circumference or substantially all of the circumference of the proximal stent 20. In some instances the suture 60 may be tied, knotted or otherwise secured to itself at the juncture of the circumferential portion of the first suture loop 64 and the connecting suture portion 68. The first end 70 of the suture 60 may then be advanced distally through or alongside the proximal stent 20 and the proximal sleeve 36 until it reaches the proximal end region 32 of the distal stent 28, thus forming the connecting suture portion 68. It is contemplated that the connecting suture portion 68 may extend along an outer surface of the proximal stent 20 and proximal sleeve 36 or along an inner surface (e.g., within the lumen 48) of the proximal stent 20 and the proximal sleeve 36, as desired. The first end 70 of the suture 60 may then be interwoven through the stent frame 30 adjacent to the proximal end region 32 of the distal stent 28 until extends about the circumference or substantially all of the circumference of the distal stent 28. The first end 70 of the suture 60 may then be knotted, tied, or otherwise secured to itself or the distal stent 28. The second end 72 of the suture 60 may be looped or knotted to form the retrieval suture loop 62.

Figure 7:
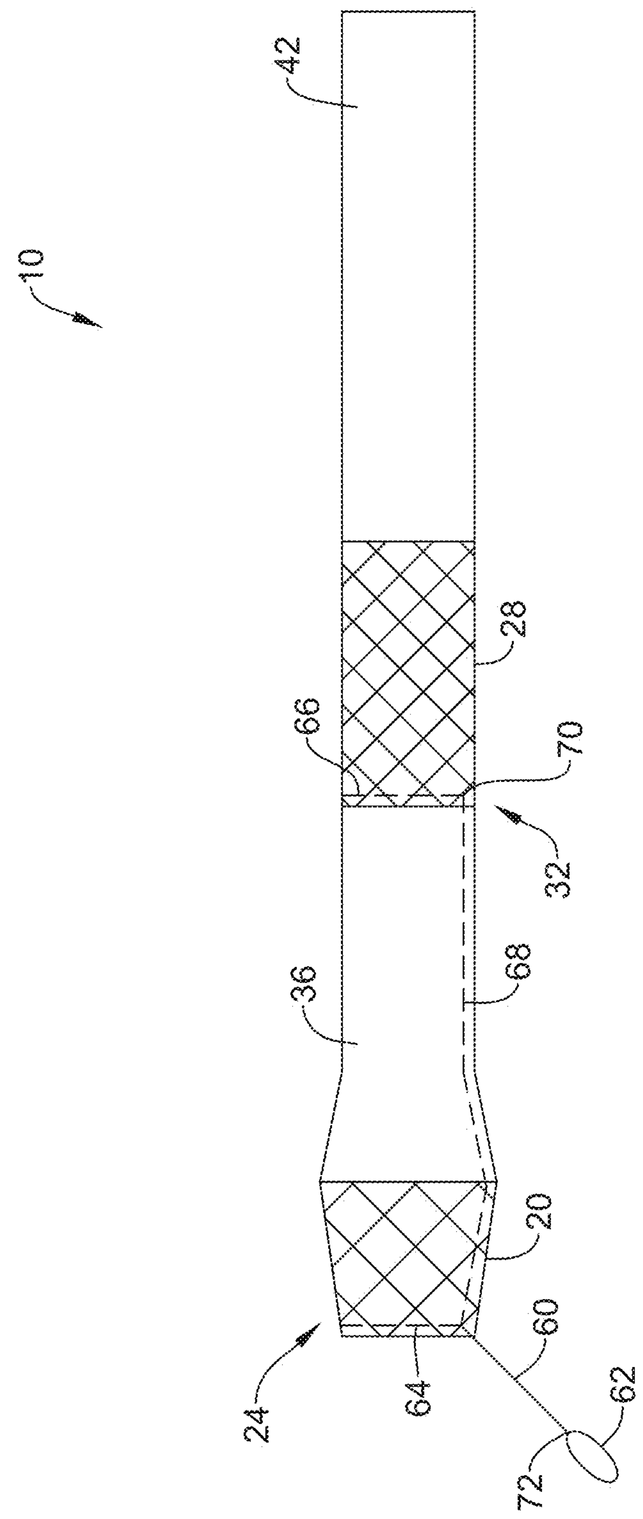
FIG. 7 is a side view of the illustrative implant of FIG. 6 with the implant in a partially collapsed configuration.
Figure 8:
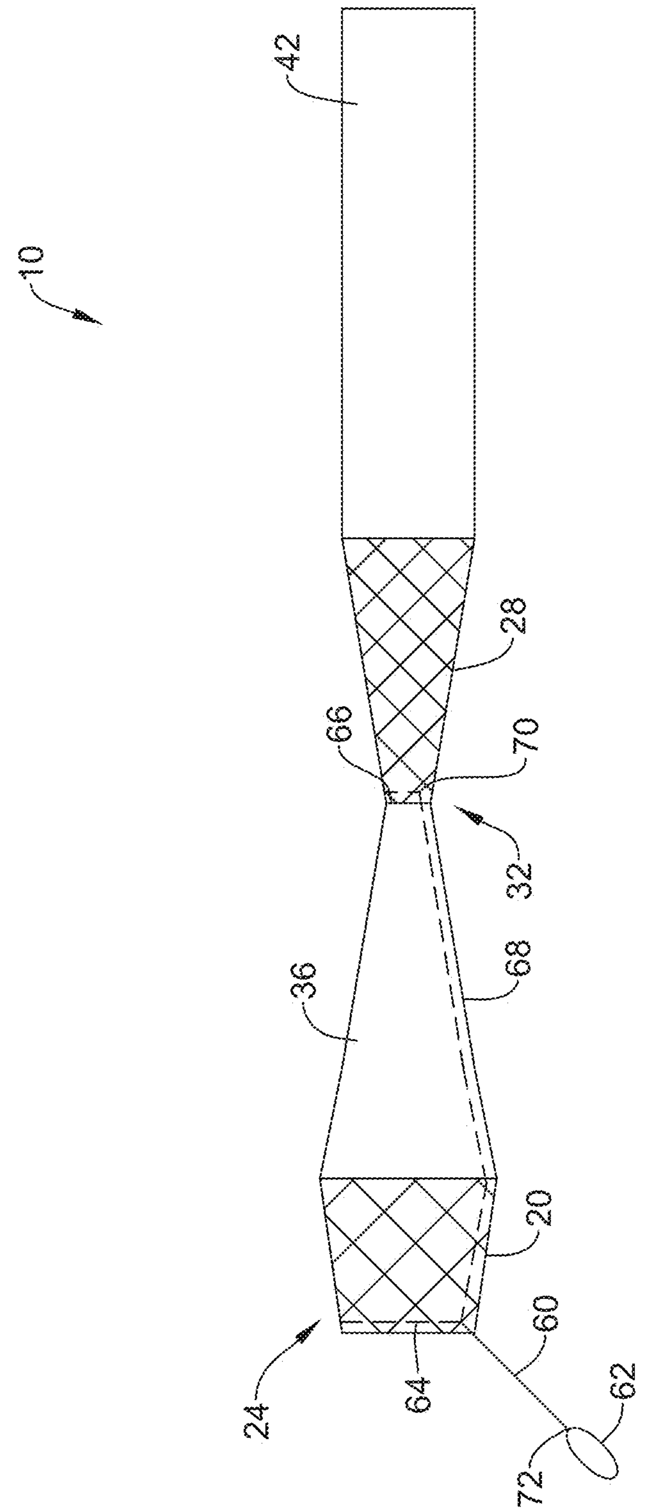
FIG. 8 is a side view of the illustrative implant of FIG. 6 with the implant in a fully collapsed configuration.

To collapse the implant 10 the retrieval suture loop 62, or the first suture loop 64 in the absence of the retrieval suture loop 62, may be pulled or otherwise actuated in a proximal direction. As the retrieval suture loop 62, or the first suture loop 64 in the absence of the retrieval suture loop 62, is pulled in the proximal direction, the first suture loop 64 begins to constrain or reduce the diameter of the proximal stent 20 as shown in FIG. 7, which illustrates a side view of the illustrative implant 10 during suture 60 actuation. It is contemplated that the length of the connecting suture portion 68 may be predetermined and selected based on both the difference in diameter of the proximal end region 24 of the proximal stent and the proximal end region 32 of the distal stent 28 and the distance between the proximal end region 24 of the first proximal stent 20 and the proximal end region 32 of the distal stent 28. The length of the connecting suture portion 68 may be greater than the distance between the first suture loop 64 and the second suture loop 66 in the deployed, expanded configuration, providing the connecting suture portion 68 slack. Thus, the length of the connecting suture portion 68 may be selected such that the first suture loop 64 is pulled to constrain the proximal end region 24 of the proximal stent 20 a first amount before the slack is taken up and the connecting suture portion 68 is pulled taut. Thereafter, further pulling on the retrieval suture loop 62, or the first suture loop 64 in the absence of the retrieval suture loop 62, causes the connecting suture portion 68 to apply a pulling force on the second suture loop 66 to begin constraining the distal stent 28. For example, the length may be selected such that when the diameter of the proximal end region 24 of the proximal stent 20 is partially constrained or reduced in diameter a first amount, the second suture loop 66 begins to constrain or reduce the diameter of the distal stent 28 adjacent the proximal end 32 thereof. The length may be selected such that when the diameter of the proximal end region 24 of the proximal stent 20 is constrained or reduced to approximately the same diameter as the distal end region 32 of the distal stent the second suture loop 66 begins to constrain a reduced diameter of the distal stent 28 adjacent the proximal end 32 thereof. In other words, the connecting suture portion 68 may include some slack or extra length that prevents the proximal actuation of the retrieval suture loop 62 from actuating the second suture loop 66 until after the first suture loop 64 has been at least partially constrained. Continued proximal actuation of the retrieval suture loop 62 once the proximal end region 24 of the proximal stent 20 has been partially constrained (e.g., is approximately equal in diameter to the proximal end region 32 of the distal stent 28) will cause both the proximal stent 20 and the distal stent 28 to reduce in diameter or constrain at approximately the same rate at the same time, as shown in FIG. 8, which illustrates a side view of the illustrative implant 10 with the implant 10 in a fully constrained configuration. This may allow for a smooth and easy repositioning or removal. However, in some embodiments, the length of the connecting suture portion 68 may be selected such that the proximal end regions 24, 32 of the proximal and distal stents 20, 28 are configured to collapse the reducing profile at approximately the same time.

Figure 9:
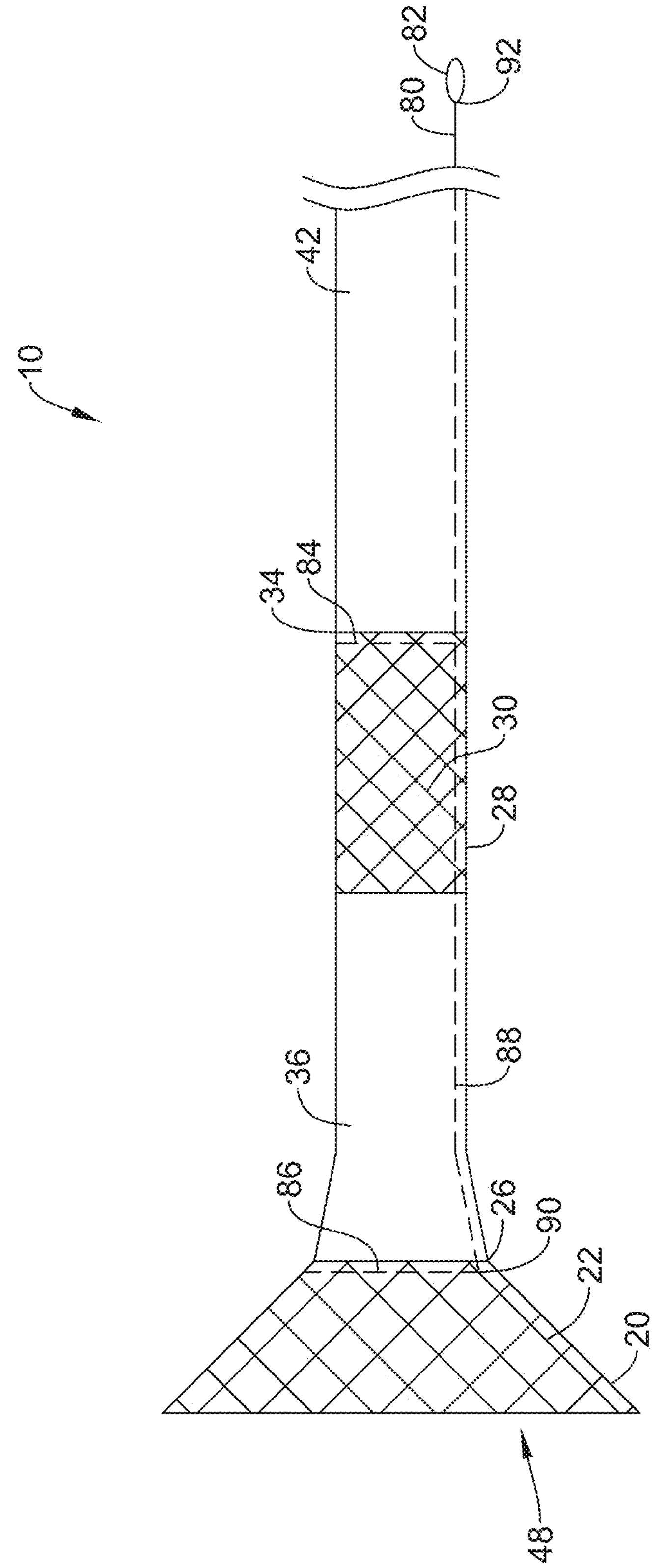
FIG. 9 is a side view of the illustrative implant of FIG. 1 with a retrieval suture in a second configuration.

FIG. 9 illustrates a side view of the illustrative implant 10 of FIG. 1 including an alternative retrieval suture 80. In order to collapse both the proximal stent 20 and the distal stent 28, the suture 80 may include a plurality of components or regions each configured to perform a function. A first region of the suture 80 may be a retrieval suture loop 82 which may be configured to be grasped by forceps or another tool during a clinical procedure for stent removal or repositioning. A second region of the suture 80 may include a first suture loop 84 which is interwoven within the distal end region 34 of the distal stent 28. The first suture loop 84 may be configured to reduce a profile of the distal stent 28 from its deployed configuration. A third region of the suture 80 may include a second suture loop 86 which is interwoven through the distal end region 26 of the proximal stent 20. The second suture loop 86 may be configured to reduce the profile of the proximal stent 20 from its deployed configuration. A fourth region of the suture 80 may include a connecting suture portion 88 that extends between and couples the first suture loop 84 and the second suture loop 86. The connecting suture portion 88 may be configured to couple the first suture loop 84 and the second suture loop 86 such that actuation of the retrieval suture loop 82 is translated to both the first suture loop 84 and the second suture loop 86.

The suture 80 may be formed from a length of material having a first end 90 and a second end 72. The length of material may be one long continuous unitary structure or a plurality of structures coupled together, as desired. To assemble the suture 80 with the implant 10, the first end 90 may be interwoven through the stent frame 30 adjacent the distal end region 34 of the distal stent 28 until it extends about the circumference or substantially all of the circumference of the distal stent 28. In some instances the suture 80 may be tied, knotted or otherwise secured to itself at the juncture of the circumferential portion of the first suture loop 84 and the connecting suture portion 88. The first end 90 of the suture 80 may then be advanced proximally through the distal stent 28 and the proximal sleeve 36 until it reaches the distal end region 26 of the proximal stent 20, thus forming the connecting suture portion 88. It is contemplated that the connecting suture portion 88 may extend along an outer surface of the distal stent 28 and proximal sleeve 36 or along an inner surface (e.g., within the lumen 48) of the distal stent 28 and the proximal sleeve 36, as desired. The first end 90 of the suture 80 may then be interwoven through the stent frame 22 adjacent to the distal end region 26 of the proximal stent 20 until extends about the circumference or substantially all of the circumference of the proximal stent 20. The first end 90 of the suture 80 may then be knotted, tied, or otherwise secured to itself or the proximal stent 20. The second end 92 of the suture 80 may be looped or knotted to form the retrieval suture loop 82.

Figure 10:
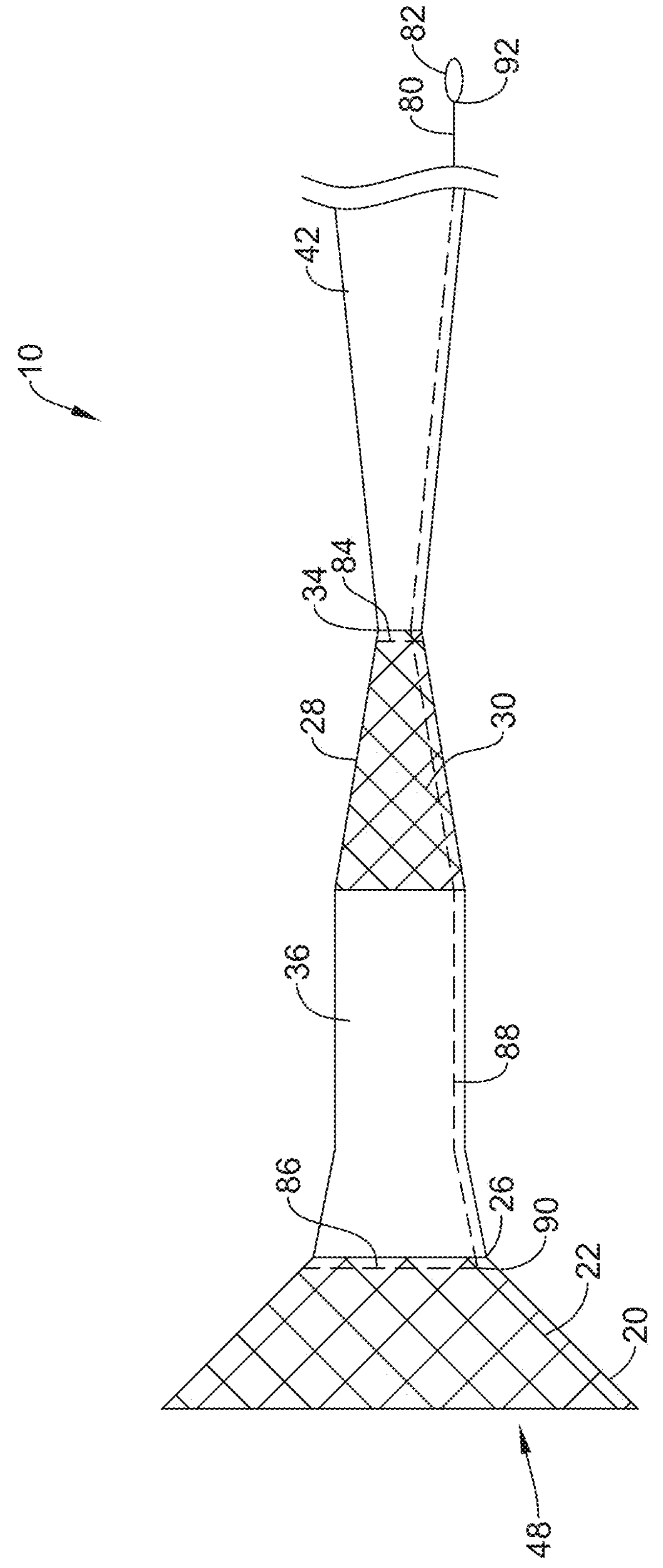
FIG. 10 is a side view of the illustrative implant of FIG. 9 with the implant in a partially collapsed configuration.
Figure 11:
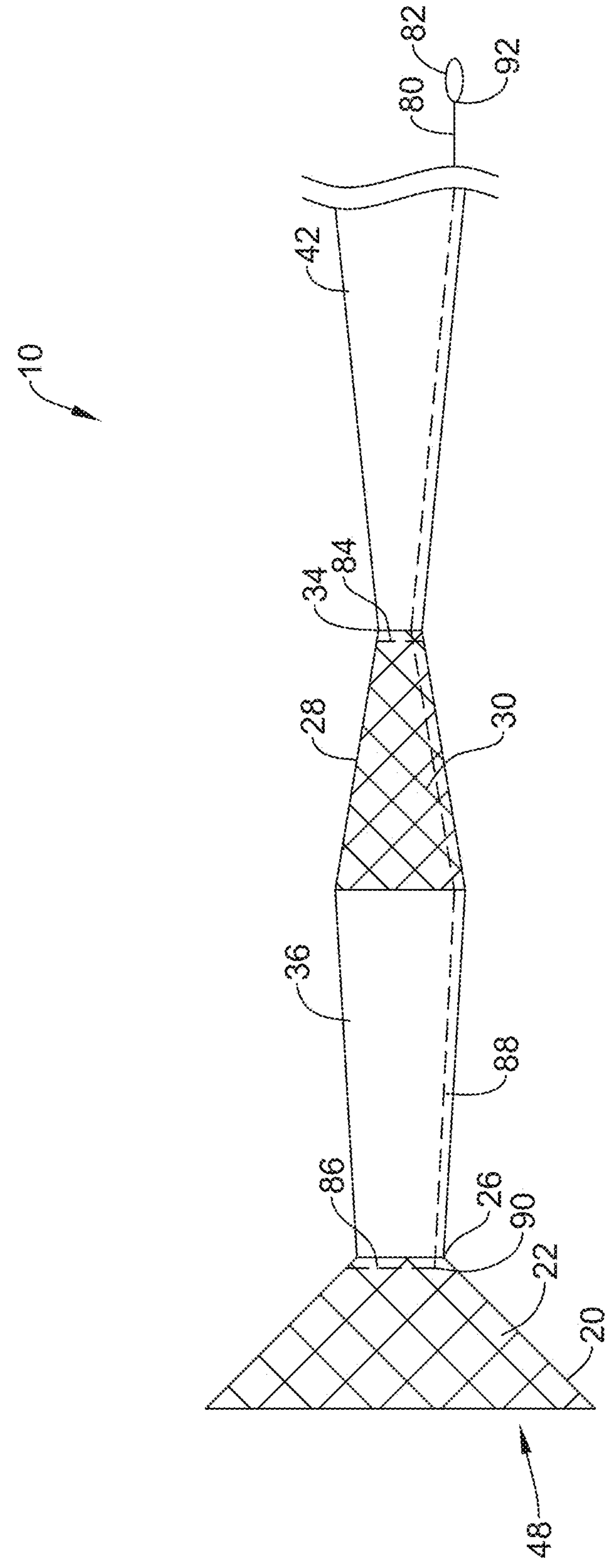
FIG. 11 is a side view of the illustrative implant of FIG. 9 with the implant in a fully collapsed configuration.

To collapse the implant 10 the retrieval suture loop 82 may be pushed or otherwise actuated in a distal direction. It is contemplated the device may be advanced through the lumen 48 to execute the distal force required to actuate the retrieval suture loop 82 in a distal direction. As the retrieval suture loop 82 is pushed in the distal direction, the first suture loop 84 begins to constrain or reduce the diameter of the distal stent 28 as shown in FIG. 10, which illustrates a side view of the illustrative implant 10 during suture 80 actuation. It is contemplated that the length of the connecting suture portion 88 may be predetermined and selected based on both the difference in diameter of the distal end region 34 of the distal stent 28 and the distal end region 26 of the proximal stent 20 and the distance between the distal end region 34 of the distal stent 28 and the distal end region 26 of the proximal stent 20. The length of the connecting suture portion 88 may be greater than the distance between the first suture loop 84 and the second suture loop 86 in the deployed, expanded configuration, providing the connecting suture portion 88 slack. Thus, the length of the connecting suture portion 88 may be selected such that the first suture loop 84 is pulled to constrain the distal end region 34 of the distal stent 28 a first amount before the slack is taken up and the connecting suture portion 88 is pulled taut. Thereafter, further pulling on the retrieval suture loop 82 causes the connecting suture portion 88 to apply a pulling force on the second suture loop 86 to begin constraining the proximal stent 20. For example, the length may be selected such that when the diameter of the distal end region 34 of the distal stent 28 is partially constrained or reduced in diameter a first amount, the second suture loop 86 begins to constrain or reduce the diameter of the proximal stent 20 adjacent the distal end 26 thereof. The length may be selected such that the distal stent 28 is reduced in profile or diameter, at least in part, prior to reducing a diameter or profile of the distal end region 26 of the proximal stent 20. In other words, the connecting suture portion 88 may include some slack or extra length that prevents the distal actuation of the retrieval suture loop 82 from actuating the second suture loop 66 until after first suture loop 84 has been at least partially constrained. Continued distal actuation of the retrieval suture loop 82 after any slack in the connecting suture portion 88 has been consumed through distal actuation will cause both the proximal stent 20 and the distal stent 28 to reduce in diameter or constrain at approximately the same rate at the same time, as shown in FIG. 11, which illustrates a side view of the illustrative implant 10 with the implant 10 in a fully constrained configuration. This may allow for a smooth and easy repositioning or removal in a distal direction. However, in some embodiments, the length of the connecting suture portion 88 may be selected such that the distal end regions 26, 34 of the proximal and distal stents 20, 28 are configured to collapse the reducing profile at approximately the same time.

While not explicitly shown, it is contemplated that the implant 10 may be provided with two or more sutures or suture patterns that allow the clinician to select which stent 20, 28 (and/or region of the stent 20, 28) is collapsed first. For example, the implant 10 may include both the suture configuration 60 illustrated in FIGS. 6-8 and the suture configuration 80 illustrated in FIGS. 9-11.

Figure 12:
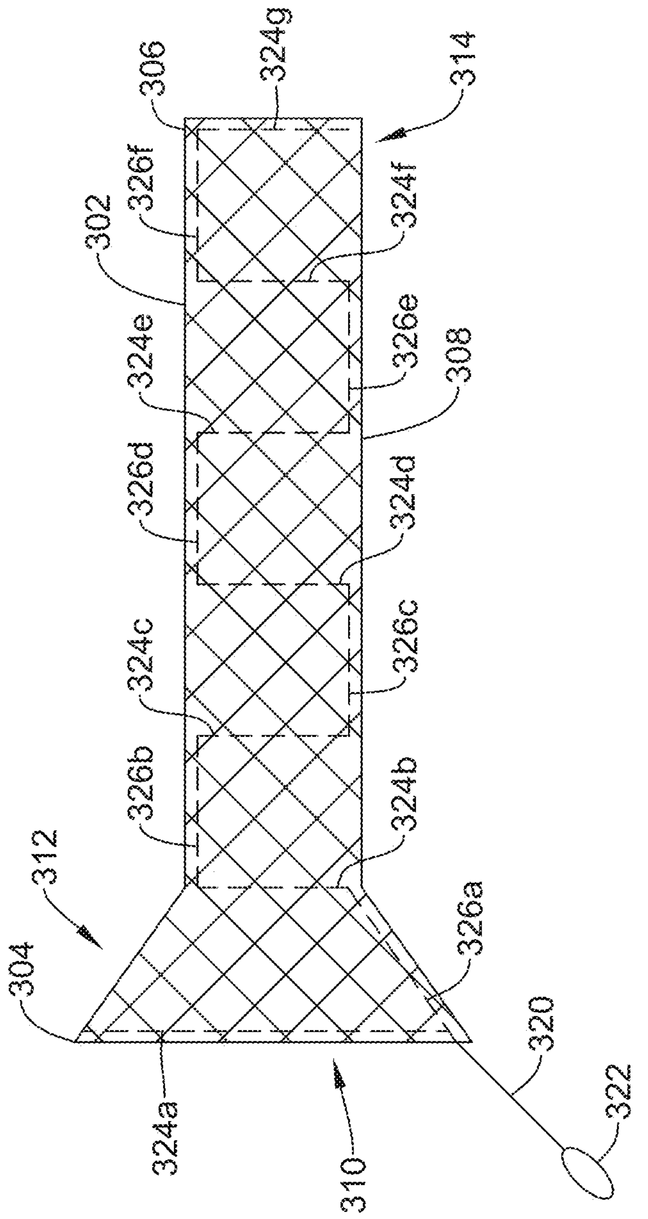
FIG. 12 is a side view of another illustrative implant a retrieval suture.

FIG. 12 illustrates a side view of another illustrative implant 300. FIG. 302 illustrates a side view of another illustrative implant 300, such as, but not limited to, a stent. In some instances, the stent 300 may be formed from an elongated tubular stent frame 302. While the stent 300 is described as generally tubular, it is contemplated that the stent 300 may take any cross-sectional shape desired. The stent 300 may have a first, or proximal end 304, a second, or distal end 306, and an intermediate region 308 disposed between the first end 304 and the second end 306. The stent 300 may include a lumen 310 extending from a first opening adjacent the first end 304 to a second opening adjacent to the second end 306 to allow for the passage of food, fluids, etc.

The stent 300 may be expandable from a first radially collapsed configuration (not explicitly shown) to a second radially expanded configuration. In some cases, the stent 300 may be deployed to a configuration between the collapsed configuration and a fully expanded configuration. The stent 300 may be structured to extend across a stricture and to apply a radially outward pressure to the stricture in a lumen to open the lumen and allow for the passage of foods, fluids, air, etc.

The stent frame 302 may have a woven structure, fabricated from a number of filaments. In some embodiments, the stent frames 22, 30 may be braided with one filament. In other embodiments, the stent frame 302 may be braided with several filaments, as is found, for example, in the WALLFLEX®, WALLSTENT®, and POLYFLEX® stents, made and distributed by Boston Scientific Corp. In another embodiment, the stent frame 302 may be knitted, such as the ULTRAFLEX™ stents made by Boston Scientific Corp. In yet another embodiment, the stent frame 302 may be of a knotted type, such the PRECISION COLONIC™ stents made by Boston Scientific Corp. In still another embodiment, the stent frame 302 may be laser cut, such as the EPIC™ stents made by Boston Scientific Corp.

It is contemplated that the stent 300 can be made from a number of different materials such as, but not limited to, metals, metal alloys, shape memory alloys and/or polymers, as desired, enabling the stent 300 to be expanded into shape when accurately positioned within the body. In some instances, the material may be selected to enable the stent 300 to be removed with relative case as well. For example, the stent 300 can be formed from alloys such as, but not limited to, Nitinol and ELGILOY®. Depending on the material selected for construction, the stent 300 may be self-expanding (i.e., configured to automatically radially expand when unconstrained). In some embodiments, fibers may be used to make the stent 300, which may be composite fibers, for example, having an outer shell made of Nitinol having a platinum core. It is further contemplated the stent 300 may be formed from polymers including, but not limited to, polyethylene terephthalate (PET). In some embodiments, the stent 300 may be self-expanding while in other embodiments, the stent 300 may be expand by an expansion device (such as, but not limited to a balloon inserted within the lumen 310 of the stent 300). As used herein the term "self-expanding" refers to the tendency of the stent to return to a preprogrammed diameter when unrestrained from an external biasing force (for example, but not limited to a delivery catheter or sheath). The stent 300 may include a one-way valve, such as an elastomeric slit valve or duck bill valve, positioned within the lumen 310 thereof to prevent retrograde flow of gastrointestinal fluids.

In some instances, in the radially expanded configuration, the stent 300 may include a first end region 312 proximate the proximal end 304 and a second end region 314 proximate the second end 306. In some embodiments, the first end region 312 and the second end region 314 may include retention features or anti-migration flared regions (not explicitly shown at the second end region 314) having enlarged diameters relative to the intermediate portion 308. The anti-migration flared regions, which may be positioned adjacent to the first end 304 and the second end 306 of the stent 300, may be configured to engage an interior portion of the walls of the esophagus, stomach or other body lumen. In some embodiments, the retention features, or flared regions may have a larger diameter than the cylindrical intermediate region 308 of the stent 300 to prevent the stent 300 from migrating once placed in the esophagus, stomach, or other body lumen. It is contemplated that a transition from the cross-sectional area of the intermediate region 308 to the retention features or flared regions may be gradual, sloped, or occur in an abrupt step-wise manner, as desired. In other embodiments, the stent 300 may have a uniform diameter from the proximal end 304 to the distal end 306.

It is contemplated that the stent 300 can be made from a number of different materials such as, but not limited to, metals, metal alloys, shape memory alloys and/or polymers, as desired, enabling the stent 300 to be expanded into shape when accurately positioned within the body. In some instances, the material may be selected to enable the stent 300 to be removed with relative case as well. For example, the stent 300 can be formed from alloys such as, but not limited to, Nitinol and ELGILOY®. Depending on the material selected for construction, the stent 300 may be self-expanding or require an external force to expand the stent 300. In some embodiments, composite filaments may be used to make the stent 300, which may include, for example, an outer shell or cladding made of Nitinol and a core formed of platinum or other radiopaque material. It is further contemplated the stent 300 may be formed from polymers including, but not limited to, polyethylene terephthalate (PET). In some instances, the filaments of the stent 300, or portions thereof, may be bioabsorbable or biodegradable, while in other instances the filaments of the stent 300, or portions thereof, may be biostable.

The implant 300 may be may be entirely, substantially or partially, covered with a polymeric covering, such as a coating (not explicitly shown). The covering may be disposed on an inner surface and/or outer surface of the implant 300, as desired. When so provided a polymeric covering may reduce or eliminate tissue ingrowth and/or reduce food impaction.

The implant 300 may further include a retrieval suture 320. The suture 320 may include a retrieval suture loop 322 which may be configured to be grasped by forceps or other tool during a clinical procedure for stent removal and or repositioning. The suture 320 may be interwoven with the stent frame 302 at intervals along a length of the implant 300 to create a plurality of suture loops 324*a*, 324*b*, 324*c*, 324*d*, 324*c*, 324*f*, 324*g* (collectively, 324). Each of the suture loops 324 may extend entirely around the circumference of the stent frame 302. It is contemplated that the suture loops 324 may be positioned at regular or even intervals throughout the overall length of the implant 300. However, in other embodiments, the suture loops 324 may be positioned at eccentric or uneven intervals along the length of the implant 300, as desired. Adjacent suture loops 324 may be connected with a longitudinal length of the suture 320 extending therebetween. For example, adjacent suture loops 324 may be connected with the suture connection links 326*a*, 326*b*, 326*c*, 326*d*, 326*e*, 326*f* (collectively, 326) such that actuation of the retrieval suture loop 322 is translated to each of the individual suture loops 324 via the longitudinally extending suture connection links 326 between each successive suture loop 324 along the length of the implant 300.

Figure 13:
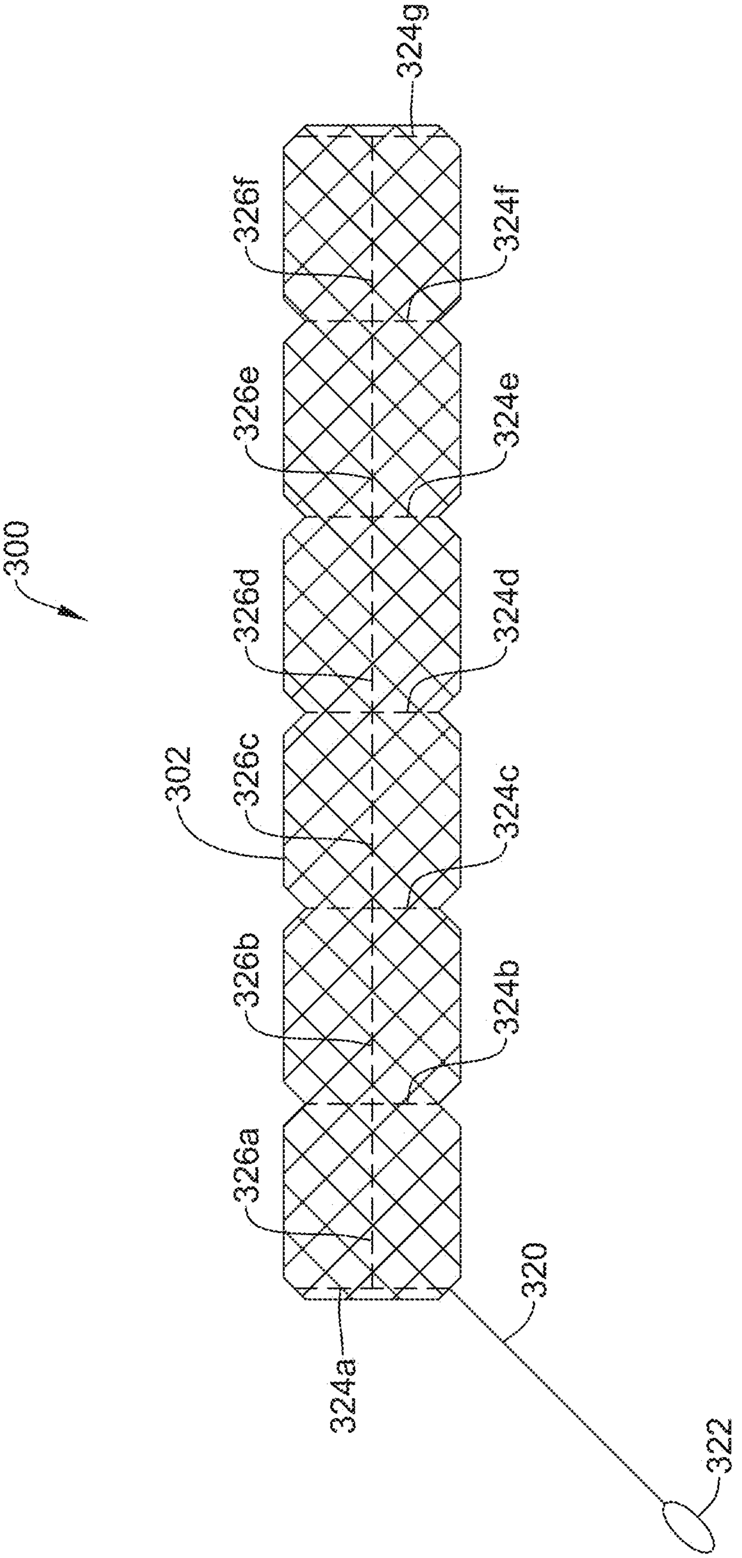
FIG. 13 is a side view of the illustrative implant of FIG. 12 with the implant in a partially collapsed configuration.
Figure 14:
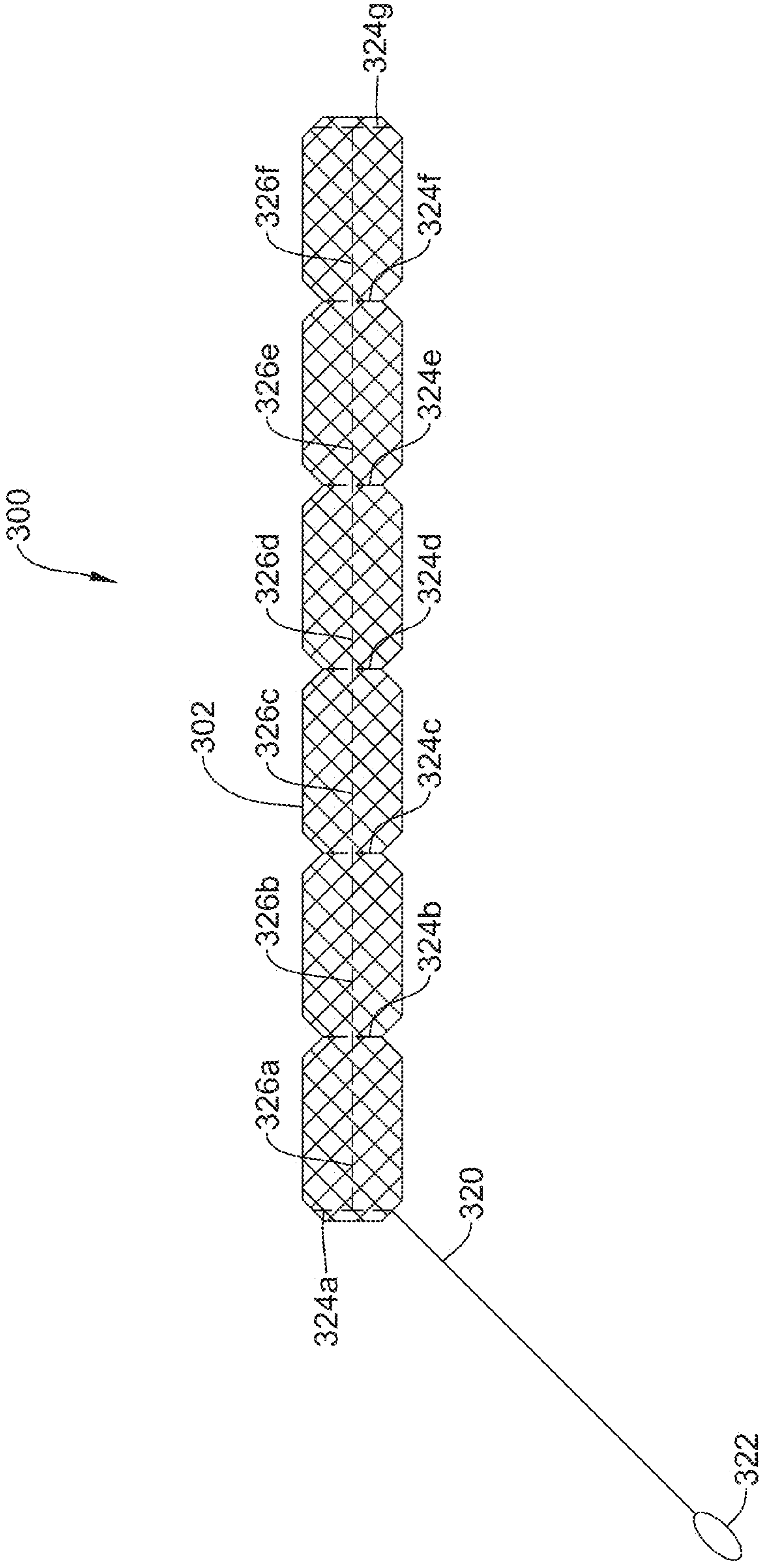
FIG. 14 is a side view of the illustrative implant of FIG. 12 with the implant in a fully collapsed configuration.

To collapse the implant 300, the retrieval suture loop 322, or the first suture loop 134*a* in the absence of the retrieval suture loop 322, may be pulled or otherwise actuated in a proximal direction. It is contemplated that the direction of actuation (e.g., proximal or distal) required to actuate the suture 320 may be dependent on the direction in which the suture 320 is interwoven with the stent frame 302. As the retrieval suture loop 322, or the first suture loop 134*a* in the absence of the retrieval suture loop 322, is actuated, the suture loops 324 begin to constrain or reduce the diameter of the implant 300, as shown in FIG. 13, which illustrates a side view of the illustrative implant 300 during suture 320 actuation. In some instances, the connection links 326 may have a length such that the suture loops 324 simultaneously (or approximately simultaneously) constrain the implant 300 along its length. However, this is not required. In some instances, the connection links 326 may have a length such that the suture loops 324 are sequentially actuated. For example, the next sequential suture loop 324 may not be actuated until the slack is removed from the preceding longitudinally extending suture connection link 326 and the suture connection link 326 is drawn taut to apply a force to the next suture loop 324. Continued actuation of the retrieval suture loop 322 may cause the implant 300 to be further reduced diameter, as shown at FIG. 14, which illustrates a side view of the illustrative implant 300 with the implant 300 in a fully constrained configuration. It is contemplated that simultaneous constrainment of the suture loops 324 may reduce the delay time between the actuation of the retrieval suture loop 322 and movement of the implant 300 during repositioning or removal. This may allow the implant 300 to be repositioned and/or removed with minimal impact on a vessel wall.

The materials that can be used for the various components of the implants 10, 100, 150, 200, 250, 300 (and variations, systems or components thereof disclosed herein) and the various elements thereof disclosed herein may include those commonly associated with medical devices. For simplicity purposes, the following discussion makes reference to the implants 10, 100, 150, 200, 250, 300 (and variations, systems or components disclosed herein). However, this is not intended to limit the devices and methods described herein, as the discussion may be applied to other elements, members, components, or devices disclosed herein.

The implants 10, 100, 150, 200, 250, 300 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-clastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super clastic varieties, may exhibit distinct and useful mechanical properties. Linear elastic and/or non-super-clastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-clastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear clastic and/or non-super-elastic nitinol may also be termed "substantially" linear elastic and/or non-super-elastic nitinol.

In some cases, linear elastic and/or non-super-clastic nitinol may also be distinguishable from super elastic nitinol in that linear elastic and/or non-super-elastic nitinol may accept up to about 2-5% strain while remaining substantially elastic (e.g., before plastically deforming) whereas super clastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about-60 degrees Celsius (C) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear clastic and/or non-super-elastic nickel-titanium alloy maintains its linear clastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of implants 10, 100, 150, 200, 250, 300 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of implants 10, 100, 150, 200, 250, 300 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of implants 10, 100, 150, 200, 250, 300 to achieve the same result.

In some embodiments, a degree of Magnetic Resonance Imaging (MRI) compatibility is imparted into implants 10, 100, 150, 200, 250, 300. For example, implants 10, 100, 150, 200, 250, 300 or portions thereof, may be made of a material that does not substantially distort the image and create substantial artifacts (i.e., gaps in the image). Certain ferromagnetic materials, for example, may not be suitable because they may create artifacts in an MRI image. The implants 10, 100, 150, 200, 250, 300 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-NR and the like), nitinol, and the like, and others.

Some examples of suitable polymers for implants 10, 100, 150, 200, 250, 300 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will appreciate that the different embodiments of the implant described here, their mode of operation, etc., are merely representative of the environment in which the present disclosure operates. Accordingly, a variety of alternatively shaped collaborating components may also be used as a substitutive for the purpose of engaging, steering and locating the stent at a desired target site, thus, not limiting the scope of the present disclosure. Further, the disclosed implants may be adequately stretchable, extendable, and retractable, allowing for its flexible deployment. More particularly, the configurations described here may be applicable for other medical applications as well, and accordingly, a variety of other medical devices may be used in combination with the implant. Those medical devices may include biopsy forceps, scissors, lithotripters, dilators, other cautery tools, and the like.

Further, while the implant is generally described along with an exemplary rigid and flexible region(s), a variety of other configurations and arrangements may also be contemplated and conceived as well. In addition, the operations, devices, and components, described herein may be equally applicable for other purposes where a component is required to be positioned in places where a leakage needs to be avoided or other treatments are desired. Embodiments of the present disclosure are thus applicable to medical and/or non-medical environments. Further, certain aspects of the aforementioned embodiments may be selectively used in collaboration, or removed, during practice, without departing from the scope of the disclosed embodiments.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. An implant, the implant comprising:

an elongated tubular member comprising:

a first region defining a proximal end of the implant, the first region including a proximal stent frame;
a second region defining a distal end of the implant, the second region including a distal stent frame having a length extending along a longitudinal axis of the elongated tubular member; and
a retrieval suture having a distal region interwoven with the distal stent frame along the length of the distal stent frame, and a proximal region interwoven with the proximal stent frame, the retrieval suture defining a plurality of spaced apart suture loops connected by a plurality of longitudinal sections, wherein the plurality of longitudinal sections each have a slack portion configured such when a first suture loop is constrained to reduce the diameter of the distal stent frame, an adjacent suture loop is not actuated until the slack portion is taken up from a preceding longitudinal section wherein distal actuation of the retrieval suture sequentially constrains the plurality of spaced apart suture loops to sequentially constrain the distal and proximal stent frames, such that distal actuation of the retrieval suture first reduces a diameter of the distal stent frame and after the diameter of the distal stent frame is at least partially reduced, further distal actuation of the retrieval suture constrains the proximal stent frame.

2. The implant of claim 1, wherein the plurality of spaced apart suture loops includes a first suture loop interwoven within a distal end region of the distal stent frame.

3. The implant of claim 2, wherein the plurality of spaced apart suture loops includes a second suture loop interwoven within a distal end region of the proximal stent frame.

4. The implant of claim 3, wherein the proximal stent frame has a flared proximal end tapering radially inward toward a distal end of the proximal stent frame.

5. The implant of claim 4, wherein the distal stent frame has an outer diameter less than an outer diameter of the flared proximal end of the proximal stent frame.

6. The implant of claim 4, wherein when the elongated tubular member is in a fully constrained configuration, the flared proximal end of the proximal stent frame is not constrained.

7. The implant of claim 1, wherein the retrieval suture is a single long continuous length of material.

8. The implant of claim 1, wherein each of the plurality of spaced apart suture loops extends entirely around a circumference of the distal stent frame and/or the proximal stent frame.

9. The implant of claim 1, wherein a length of each of the plurality of longitudinal sections is greater than a distance between adjacent suture loops.

10. An implant, the implant comprising:

an elongated tubular member comprising:

a first region defining a proximal end of the implant, the first region including a proximal stent frame with a flared proximal end tapering radially inward to a distal end of the proximal stent frame;
a second region defining a distal end of the implant, the second region including a distal stent frame having a length extending along a longitudinal axis of the elongated tubular member; and
a retrieval suture having a distal end defining a retrieval suture loop, a distal region interwoven along the length of the distal stent frame, and a proximal region interwoven with the proximal stent frame, the retrieval suture defining a plurality of spaced apart suture loops connected by a plurality of longitudinal sections, wherein the plurality of spaced apart suture loops includes a first suture loop interwoven with a distal end region of the distal stent frame and a second suture loop interwoven within a distal end region of the proximal stent frame; wherein the first longitudinal section of the retrieval suture extending along the flexible sleeve has a slack portion configured such when the first suture loop is constrained to reduce a diameter of the distal stent frame, the second suture loop is not actuated until the slack portion is taken up wherein distal actuation of the retrieval suture sequentially constrains the plurality of spaced apart suture loops to sequentially constrain first the distal and then the proximal stent frames;

wherein the first region includes a flexible sleeve extending between the proximal stent frame and the distal stent frame, wherein a first longitudinal section of the plurality of longitudinal sections of the retrieval suture extends along a length of the flexible sleeve.

11. The implant of claim 10, wherein distal actuation of the retrieval suture first reduces a diameter of the distal stent frame and after the diameter of the distal stent frame is at least partially reduced, further distal actuation of the retrieval suture constrains the proximal stent frame.

12. The implant of claim 10, wherein when in a fully collapsed configuration, the flared proximal end of the proximal stent frame is not constrained.

13. The implant of claim 10, wherein the retrieval suture is a single long continuous length of material.

14. The implant of claim 10, wherein each of the plurality of spaced apart suture loops extends entirely around a circumference of the distal stent frame and/or the proximal stent frame.

15. The implant of claim 10, wherein a length of each of the plurality of longitudinal sections is greater than a distance between adjacent suture loops.

16. An implant, the implant comprising:

an elongated tubular member comprising:

a first region defining a proximal end of the implant, the first region including a proximal stent frame with a flared proximal end tapering radially inward to a distal end of the proximal stent frame;
a second region defining a distal end of the implant, the second region including a distal stent frame having a length extending along a longitudinal axis of the elongated tubular member; and
a retrieval suture having a distal region interwoven along the length of the distal stent frame, and a proximal region interwoven with the proximal stent frame, the retrieval suture defining a plurality of spaced apart suture loops connected by a plurality of longitudinal sections, wherein distal actuation of the retrieval suture sequentially constrains the plurality of spaced apart suture loops to sequentially constrain the distal stent frame and the proximal stent frame, wherein the plurality of longitudinal sections each have a slack portion configured such that when a first suture loop is constrained to reduce a diameter of the distal stent frame, an adjacent suture loop is not actuated until the slack portion is taken up from a preceding longitudinal section wherein distal actuation of the retrieval suture first reduces a diameter of the distal stent frame and after the diameter of the distal stent frame is at least partially reduced, further distal actuation of the retrieval suture constrains the proximal stent frame, wherein when the elongated tubular member is in a fully constrained configuration, the flared proximal end of the proximal stent frame is not constrained.

* * * * *